United States Patent
Likovich et al.

(10) Patent No.: US 9,933,298 B2
(45) Date of Patent: *Apr. 3, 2018

(54) MONITORING LIGHT EXPOSURE USING A WEIGHTING FUNCTION AND LIGHT-MONITORING SYSTEM CONFIGURED FOR USER COMMUNICATION

(71) Applicant: SunSprite, Cambridge, MA (US)

(72) Inventors: Edward Likovich, Boston, MA (US); Kasey J. Russell, Somerville, MA (US); Thomas C. Hayes, Cambridge, MA (US); Jacqueline Olds, Cambridge, MA (US); Richard Schwartz, Cambridge, MA (US)

(73) Assignee: SunSprite, Cambridge, MA (US)

( * ) Notice: Subject to any disclaimer, the term of this patent is extended or adjusted under 35 U.S.C. 154(b) by 124 days.

This patent is subject to a terminal disclaimer.

(21) Appl. No.: 14/991,920

(22) Filed: Jan. 9, 2016

(65) Prior Publication Data

US 2016/0123802 A1 May 5, 2016

Related U.S. Application Data

(63) Continuation of application No. PCT/US2014/046293, filed on Jul. 11, 2014, which is
(Continued)

(51) Int. Cl.
*G01J 1/42* (2006.01)
*G01J 1/02* (2006.01)
(Continued)

(52) U.S. Cl.
CPC .......... *G01J 1/4204* (2013.01); *A61B 5/4857* (2013.01); *A61B 5/6898* (2013.01);
(Continued)

(58) Field of Classification Search
CPC .......... H01L 67/18; H01L 67/22; H01J 31/26; A61B 5/681; A61B 5/0002; A61B 5/02438; A61B 5/14552
See application file for complete search history.

(56) References Cited

U.S. PATENT DOCUMENTS 3,268,839 A   8/1966   McFarland
3,878,496 A   4/1975   Erickson
(Continued)

FOREIGN PATENT DOCUMENTS

WO   2001/52736 A1   7/2001
WO   2005/103923 A2   11/2005
(Continued)

OTHER PUBLICATIONS

Chandra, et al., "Treatment of vitamin D deficiency with UV light in patients with malabsorption syndromes: a case series", 23 Photodermatol. Photoimmunol. Photomed. 179-185 (Oct. 2007).
(Continued)

*Primary Examiner* — Francis M Legasse, Jr.
(74) *Attorney, Agent, or Firm* — Modern Times Legal; Robert J. Sayre

(57) ABSTRACT

Light exposure from at least one light source is received with a light detector of a light monitor that includes at least one of (a) an output device and (b) a communication device transported by a user. The light detector converts the light exposure into an electrical signal, and the current time of day at which the light exposure is received is recorded. An instantaneous light exposure value is generated from the electrical signal, and a weighting function is applied to the instantaneous light exposure value as a function of the recorded time of day associated with the light exposure to produce a weighted instantaneous light exposure value. The weighted instantaneous light exposure value is integrated to produce a weighted cumulative luminous exposure value;
(Continued)

and the weighted cumulative luminous exposure value is compared with an established luminous-exposure target.

26 Claims, 9 Drawing Sheets

Related U.S. Application Data a continuation of application No. 13/939,217, filed on Jul. 11, 2013, now Pat. No. 9,163,983.

(60) Provisional application No. 61/943,660, filed on Feb. 24, 2014, provisional application No. 62/010,881, filed on Jun. 11, 2014.

(51) Int. Cl.
    *A61B 5/00* (2006.01)
    *G01J 1/44* (2006.01)
    *A61N 5/06* (2006.01)

(52) U.S. Cl.
    CPC .......... *A61N 5/0618* (2013.01); *G01J 1/0204* (2013.01); *G01J 1/0219* (2013.01); *G01J 1/0271* (2013.01); *G01J 1/42* (2013.01); *G01J 1/44* (2013.01); *A61N 2005/0628* (2013.01); *A61N 2005/0652* (2013.01)

(56) References Cited

U.S. PATENT DOCUMENTS

| | | | |
|---|---|---|---|
| 4,229,733 A | 10/1980 | Tulenko et al. | |
| 4,348,664 A | 9/1982 | Boschetti et al. | |
| 4,428,050 A | 1/1984 | Pellegrino et al. | |
| 4,643,568 A | 2/1987 | Forsberg | |
| 4,851,686 A | 7/1989 | Pearson | |
| 5,008,548 A | 4/1991 | Gat | |
| 5,036,311 A | 7/1991 | Moran et al. | |
| 5,151,600 A | 9/1992 | Black | |
| 5,365,068 A | 11/1994 | Dickerson | |
| 5,500,532 A | 3/1996 | Kozicki | |
| D376,547 S | 12/1996 | McRae | |
| 5,992,996 A | 11/1999 | Sawyer | |
| 6,322,503 B1 | 11/2001 | Sparhawk | |
| 6,582,380 B2 | 6/2003 | Kazlausky et al. | |
| D479,805 S | 9/2003 | Tsai | |
| 7,265,358 B2 | 9/2007 | Fontaine | |
| 7,808,392 B1 | 10/2010 | Anklesaria | |
| 7,874,666 B2 | 1/2011 | Xu et al. | |
| 8,157,730 B2 | 4/2012 | LeBoeuf et al. | |
| 8,784,271 B2 * | 7/2014 | Brumback | 340/870.16 |
| 9,163,983 B2 | 10/2015 | Olds et al. | |
| 2005/0015122 A1 * | 1/2005 | Mott | A61M 21/00 607/88 |
| 2006/0206173 A1 | 9/2006 | Gertner et al. | |
| 2008/0077199 A1 | 3/2008 | Sheffi et al. | |
| 2008/0265170 A1 | 10/2008 | Ales et al. | |
| 2009/0090865 A1 | 4/2009 | Lub et al. | |
| 2009/0318802 A1 | 12/2009 | Boyden et al. | |
| 2010/0163750 A1 | 7/2010 | Hunwick et al. | |
| 2010/0217099 A1 | 8/2010 | LeBoeuf et al. | |
| 2010/0219789 A1 | 9/2010 | Bermak et al. | |
| 2011/0133103 A1 | 6/2011 | Folkesson | |
| 2012/0226111 A1 | 9/2012 | LeBoeuf et al. | |
| 2012/0330387 A1 | 12/2012 | Rigo et al. | |
| 2013/0172963 A1 | 7/2013 | Moffat | |

FOREIGN PATENT DOCUMENTS

| | | |
|---|---|---|
| WO | 2011/089539 A1 | 7/2011 |
| WO | 2011/094742 A2 | 8/2011 |
| WO | 2013/106653 A1 | 7/2013 |

OTHER PUBLICATIONS

Rabin, Roni C. "A Portable Glow to Help Melt Those Winter Blues", New York Times (Nov. 14, 2011).
Rensselaer Lighting Research Center, "Dimesimeter—Light and Activity Measurement System Description and calibration" (Nov. 15, 2011).
Bharatula, Nagendra B., et al., "Towards Wearable Autonomous Microsystems", PERVASIVE 2004, 225-237 (2004).
NASA, "Hardware Information: Actillume", Life Sciences Data Archive, Johnson Space Center, Houston, Texas, <http://lsda.jsc.nasa.gov/cf/scripts/hardware/hw_search_start_adv.cfm> (visited Dec. 7, 2011) (Sep. 6, 2011).
US Small Business Innovation Research / Small Business Technology Transfer, "ACTILLUME—A Monitor for Activity and Light Exposure" <http://www.sbir.gov/sbirsearch/detail/86950> (visited Dec. 7, 2011).

* cited by examiner

MONITORING LIGHT EXPOSURE USING A WEIGHTING FUNCTION AND LIGHT-MONITORING SYSTEM CONFIGURED FOR USER COMMUNICATION

RELATED APPLICATION

This application is a continuation of International Application No. PCT/US2014/046293, filed on 11 Jul. 2014, with the title, "Integrative Light-Powered Light-Monitoring System," and the same inventors as named herein, which is a continuation of U.S. application Ser. No. 13/939,217, filed on 11 Jul. 2013.

This application also claims the benefit of U.S. Provisional Application No. 61/943,660, filed on 24 Feb. 2014, and the benefit of U.S. Provisional Application No. 62/010,881, filed on 11 Jun. 2014.

The entire contents of each of these applications are incorporated herein by reference.

BACKGROUND

Exposure to bright light has been demonstrated to be effective in multiple studies of bright-light therapy for seasonal and non-seasonal depression. These studies have also defined an optimal dose of light as a function of intensity and time. Light has an effect on hormones and neurotransmitters (e.g., melatonin and serotonin), which are involved in the regulation of mood, energy, and appetite.

Studies have also demonstrated that bright light can reduce insomnia associated with circadian rhythm difficulties. Light therapy may also be helpful in treating depression during pregnancy, dementia in the elderly, bulimia nervosa, severe premenstrual syndrome, attention deficit hyperactivity disorder, and bipolar disorder.

Based on these findings, psychiatrists have conducted studies and prescribed the use of artificial light boxes, requiring patients to sit in one place, indoors, and close to the light source to provide controlled means of dosing the light to the patient. Despite the known benefits, bright-light therapy is not widely prescribed by doctors, according to a recent New York Times article (R. Rabin, "A Portable Glow to Help Melt Those Winter Blues," New York Times, 14 Nov. 2011).

> Why, then, do so few doctors prescribe bright-light therapy? Some say their patients don't have the patience to sit in front of a light for 30 to 45 minutes every morning. Moreover, "doctors are just more comfortable prescribing medication, because that's what they do for everything," Dr. [Alfred] Lewy [professor of psychiatry at Oregon Health and Science University] said.

Id. Accordingly, depression therapy currently remains focused, in large part, on medication with some use of light-box therapy.

SUMMARY

A light-monitoring system and method are described herein. Various embodiments of the apparatus and method may include some or all of the elements, features and steps described below.

As described herein, light exposure from at least one light source is received with a light detector of a light monitor. The light monitor further includes at least one of (a) an output device and (b) a communication device transported by a user. The light detector converts the light exposure into an electrical signal, and the current time of day at which the light exposure is received is recorded. An instantaneous light exposure value is generated from the electrical signal, and a weighting function is applied to the instantaneous light exposure value as a function of the recorded time of day associated with the light exposure to produce a weighted instantaneous light exposure value. The weighted instantaneous light exposure value is integrated to produce a weighted cumulative luminous exposure value; and the weighted cumulative luminous exposure value is compared with an established luminous-exposure target. An indication of the weighted cumulative luminous exposure value in comparison with the established luminous-exposure target is then provided.

A light-monitoring system includes a power source; a light detector that generates an electrical signal when illuminated by light; a computer processor coupled with the power source and in communication with the light detector and configured to receive and record an indication of exposure to light from the generated electrical signal; an output device coupled with the computer processor and configured to communicate directly with a user of the light monitoring system; and a non-transitory computer-readable medium coupled with the computer processor and storing instruction code for summing the recorded indication of exposure to light from the computer processor over time and communicating a signal to the output device to generate and communicate a signal to the user of the light-monitoring system indicating that a cumulative threshold light exposure for the wearer to achieve a psychological benefit or a benefit in treating insomnia or a circadian rhythm disorder has been reached.

The apparatus and method allow for cross-mode integrated monitoring of light from various sources (e.g., light box and natural sunlight) and exposure tracking to display incremental progress toward and achievement of a targeted dose of bright light exposure, e.g., effective for the treatment of seasonal affective disorder depression (SADD). Additionally, the apparatus for performing these functions can be comparatively simple and inexpensive, readily enabling low-cost purchase by patients and independent use after diagnosis and prescription of this treatment methodology by a physician (e.g., a psychiatrist) to treat depression or other disorder.

Figure 1:
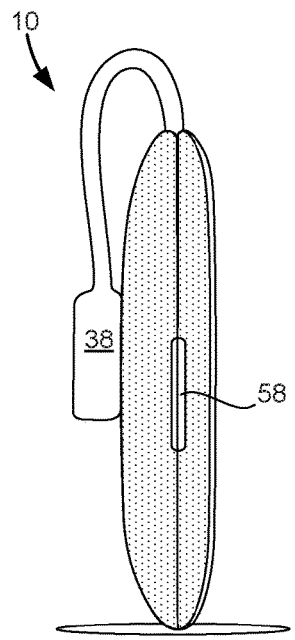
FIGS. 1-3 provide photographic images of an embodiment of the integrative light monitor from different perspectives.

In the accompanying drawings, like reference characters refer to the same or similar parts throughout the different views; and apostrophes are used to differentiate multiple instances of the same or similar items sharing the same reference numeral. The drawings are not necessarily to scale, emphasis instead being placed upon illustrating particular principles, discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular shape is referenced, the shape is intended to include imperfect variations from ideal shapes, e.g., due to manufacturing tolerances.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to" or "coupled to" another element, it may be directly on, connected or coupled to the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Figure 2:
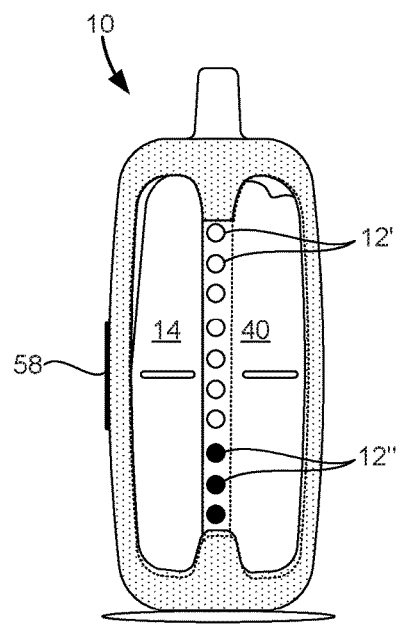
Figure 3:
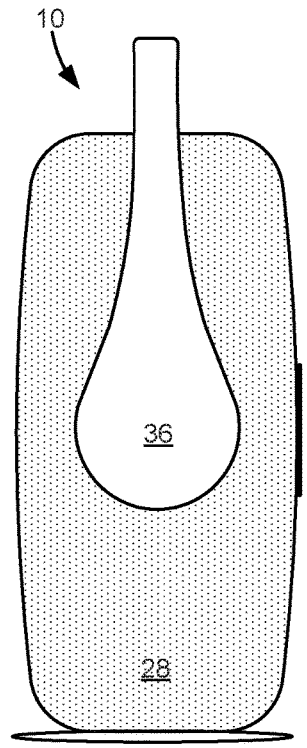
Figure 4:
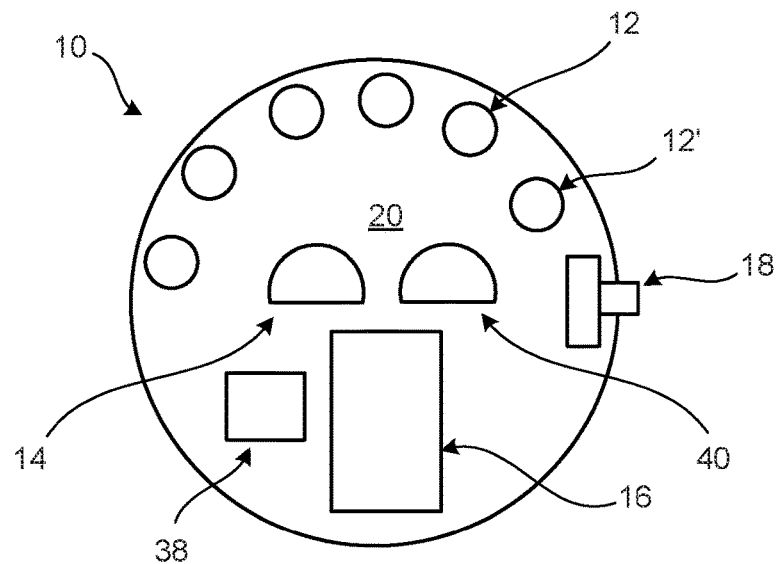
FIG. 4 is a front view of the internal components of an embodiment of an integrative light monitor including a phototransistor 14, microcontroller 16, and an output device 12 in the form of a series of LED lights.

A new design for a wearable light monitor 10 is shown in FIGS. 1-3 from left-side, front and back perspectives, respectively. An interrogation button 58 (e.g., triggering a display of cumulative exposure) is seen on the left side of the casing shown in FIG. 1; LEI) light indicators (illuminated 12' and dark 12"), used as a display to communicate with user, and a pair of light sensors 14 (here, photovoltaic cells) are shown in the front-side view of FIG. 2. Finally, as shown in FIG. 3, a magnetic clip 54 (wherein the end of the clasp secures to a magnetic material on or inside the casing) can be used to clip the light monitor 10 to the user, e.g., to a user's pocket.

Figure 5:
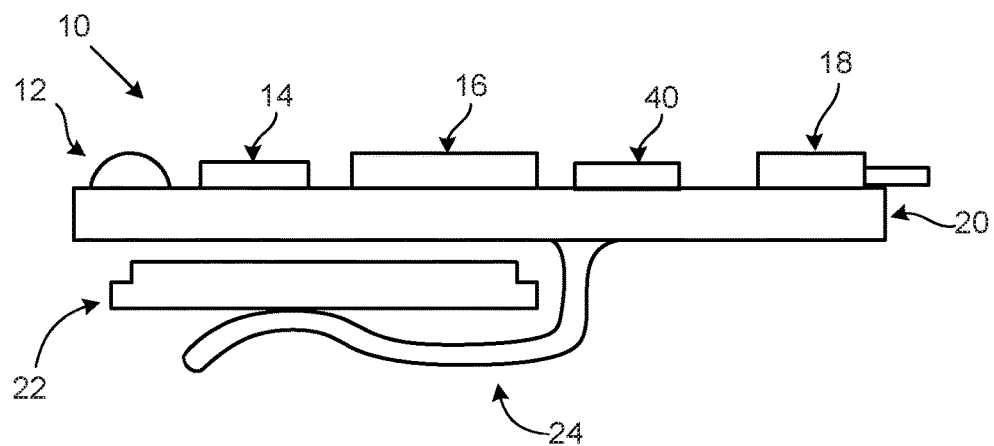
FIG. 5 is a sectional side view of the internal components of the integrative light monitor of FIG. 4, also showing the battery 22 and the printed circuit board 20 on which the integrative light monitors are mounted.

Another embodiment of the integrative light monitor 10 (shown in FIGS. 4-8) is a wearable micro light sensor that can be about the size and shape of a tie tack or a U.S. quarter, though the monitor 10 can take any of a wide variety of shapes (e.g., round, square, rectangular, oval, contorted, emblematic, etc., some of which are shown in FIGS. 10-18) and sizes. The features and components of this embodiment also can be used in the embodiment of FIGS. 1-3 and other embodiments. It can be worn attached to a wearer's clothing, much like a tie tack or pin, facing forward in the same orientation as the eyes. The integrative light monitor 10 can be powered by a solar cell and/or a battery 22 (e.g., a CR1216 coin, CR2020, CR2025, CR2032, or button cell battery or a rechargeable cell battery), as shown in FIG. 5, and can measure the intensity and duration of bright light exposure received by the wearer's eyes by being oriented approximately in the direction of the wearer's gaze. The integrative light monitor 10 can include, for example, some or all of the following components: at least one light detector 14 (e.g., a phototransistor); a power switch 18; a battery 22

(e.g., a 12, 20, 22, or 24 mm coin cell battery using a lithium compound for energy storage), which can optionally be accessible via access door 32; a processor (such as a computer microprocessor or an application-specific integrated circuit) and computer-readable memory (e.g., addressable semiconductor memory), both of which can be incorporated in a microcontroller 16; an output device 12 (e.g., a visual display, such as series of light emitting diodes); a radiofrequency wireless transmitter or an output port, such as a mini- or micro-USB port; an input device, such as a capacitive touch plate 34, a button 58, or an accelerometer 38 that can be used to evoke an indication of progress or can register input in the form, e.g., of a flick or tap by the user; a power input device for either wired or wireless recharging of a battery (e.g., a photodiode or other photovoltaic cell for wireless optical recharging, a solenoid or transformer for wireless electrical recharging, or a receptacle enabling direct electrical connection for recharging, which can be the same as the electrical port used for data transmission); and an attachment mechanism 36 (e.g., a permanent magnet and ferromagnetic material, a pin, a chain, a band, or a clip). The electronic components can all be mounted and electrically interconnected on an integrated printed circuit board 20 contained inside the integrative light monitor's transparent front housing 26 and back 28 of the case and encircled by a bezel 30 that joins the front 26 and back 28 and rotates to activate the power switch 18.

Natural light exposure (e.g., from the sun) can be used as a replacement for or in combination with light box therapy. Embodiments of light boxes designed for light box therapy are available from, for example, Light Therapy Products of Stillwater, Minn. Alternatively, other light sources can be used in combination with natural light.

In particular embodiments, the integrative light monitor 10 can have a circular disk-shaped profile and a size approximately matching that of a U.S. quarter, though perhaps thicker (e.g., with a diameter of about 2.4 cm and a thickness of about 5 mm). The integrative light monitor 10 can include a pin, clip, magnet 36, or other clasp mechanism for affixing the integrative light monitor to clothing (e.g., a shirt, belt, shoes, backpack, hat, etc.); alternatively (or in addition), the integrative light monitor can have a loop through which a string, chain, tether, etc., can be strewn so that the integrative light monitor can be worn about a wearer's neck. In other embodiments, the integrative light monitor 10 can be worn on the body of a user (e.g., wrapped around a user's wrist, incorporated into an earring and secured to a stem inserted through a user's earlobe, affixed to a ring worn on a user's finger, or affixed to a chain worn around the user's neck). In still other embodiments, the user may wear the integrative light monitor 10 on the user's body underneath clothing; and the integrative light monitor 10 can be calibrated to account for the amount of light blocked by the clothing. Moreover, the integrative light monitor 10 can be configured to accept any of a plurality of interchangeable attachment mechanisms, where the attachment mechanisms can be interchangeably pressure fit or locked into the body of the integrative light monitor 10 to allow the user to wear the integrative light monitor 10 in different ways depending on factors such as attire, environment, and activity on a particular day.

Figure 6:
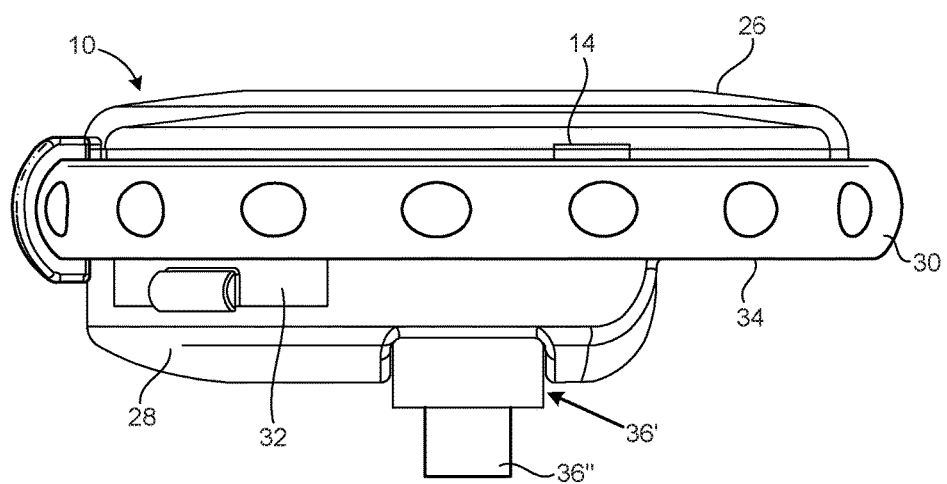
FIG. 6 is a side view of the integrative light monitor of FIGS. 2 and 3 including the outer housing halves 26 and 28 joined by bezel 30, and showing a battery access door 32 and an affixed pin 36 for attachment to clothing.
Figure 7:
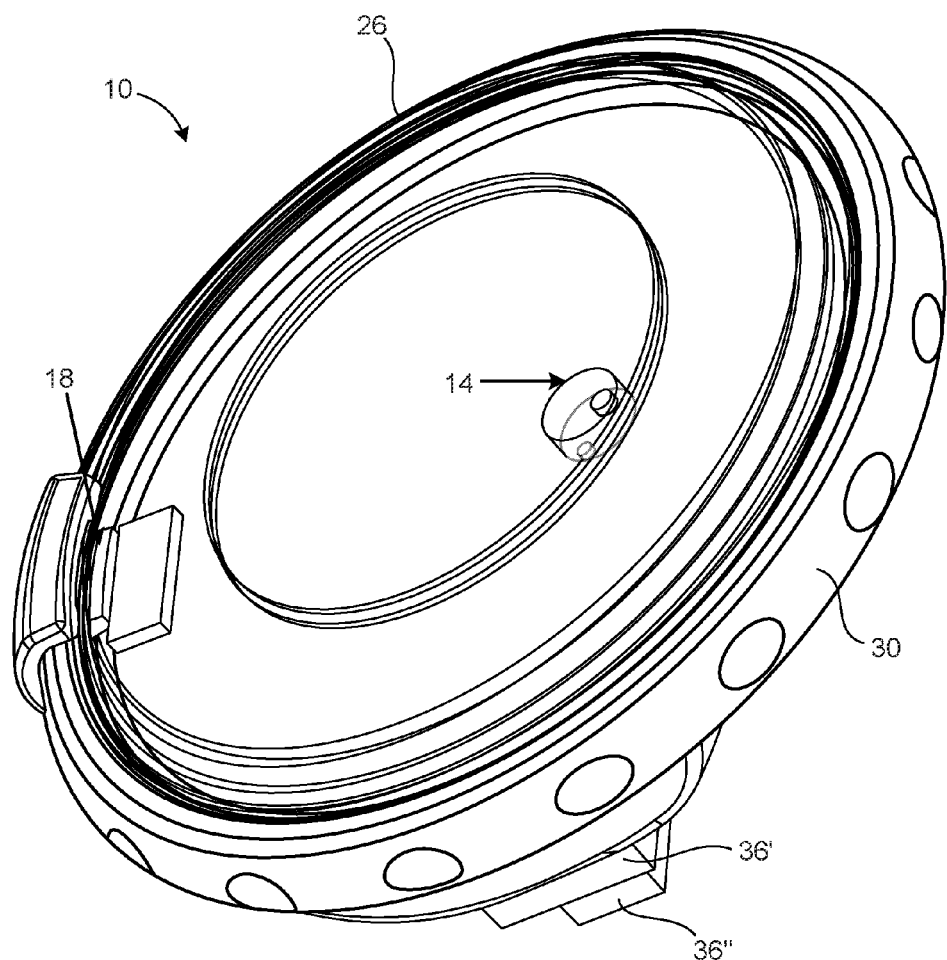
FIG. 7 is a perspective view of the top of the integrative light monitor of FIGS. 4-6.
Figure 8:
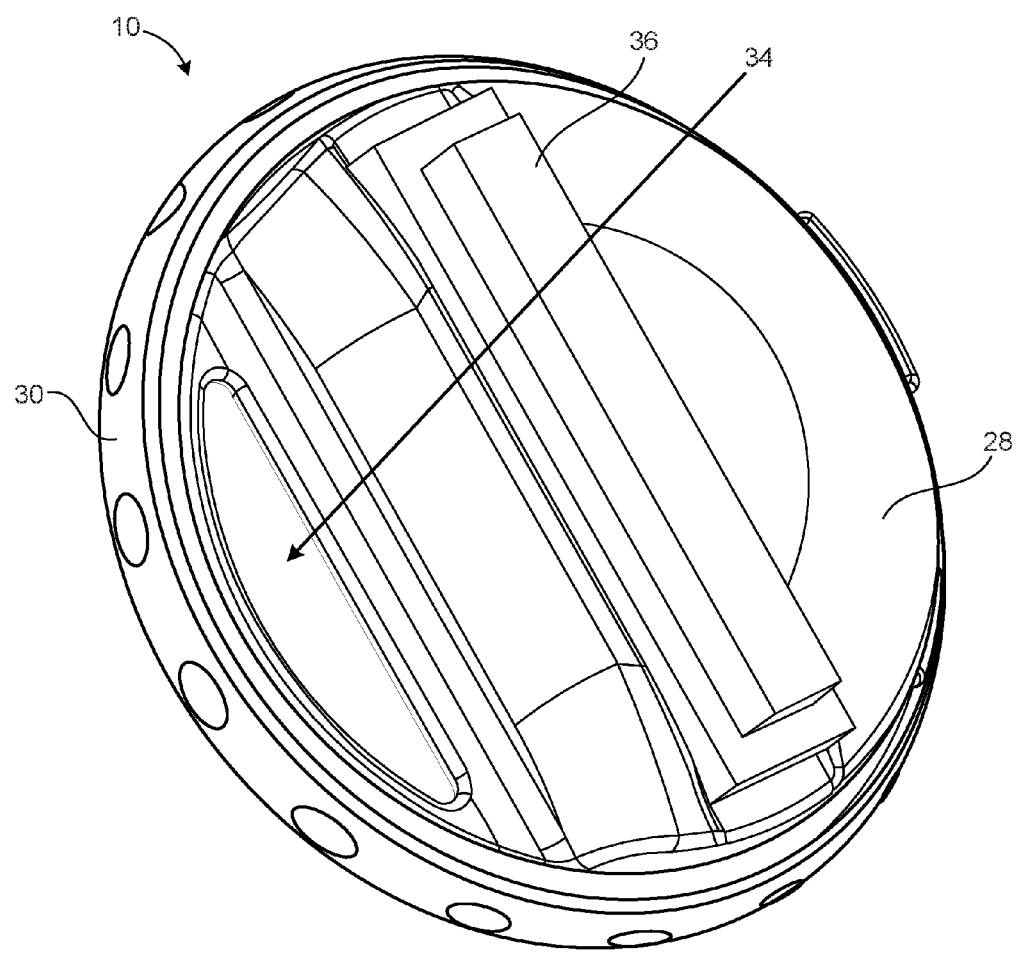
FIG. 8 is a perspective view of the back of the integrative light monitor of FIGS. 4-7.

In one embodiment, as shown in FIGS. 6 and 7, a first magnetic material 36' (e.g., a permanent magnet or a ferromagnetic material that responds to a magnetic field) is embedded into the integrative light monitor, and a second magnetic material 36" (e.g., a permanent magnet if the first magnetic material is a ferromagnetic material or vice versa) to which the first magnetic material 36' can be magnetically secured and positioned on an opposite side of clothing fabric (e.g., against the inside of a shirt pocket or opening or the underside of a collar) to allow the first magnetic material on the integrative light monitor to be magnetically secured thereto through the fabric. The first magnetic material 36' can be in the form of a flat plate of ferromagnetic material (e.g., iron, nickel, cobalt or rare-earth alloy) that is either attached to the back 28 of the integrative light monitor's packaging or embedded within the integrative light monitor's packaging. In some embodiments, the case of the battery 22, itself, can serve as the first magnetic material.

If the integrative light monitor is mounted via a magnetic attachment 36, a magnetic reed relay mounted on the printed circuit board 20 can be used to turn the integrative light monitor 10 "on" only when the first and second magnetic materials are secured to each other. In other embodiments, a bezel 30 can be provided at the perimeter of the integrative light monitor 10 and can be pivoted (rotated) along the perimeter in either direction to activate the power switch 18 to turn the power on and off.

In another embodiment, the integrative light monitor 10 can be mounted on the temple arm of a wearer's eyeglasses (e.g., non-shading prescription eyewear) with the light detector configured to face in the same direction as the wearer's eyes when wearing the eyeglasses to obtain a more accurate reading as to the light exposure at the eyes. In this embodiment, the light emitting diodes (LEDs) 12 or other display indicators can be provided in a straight-line orientation parallel to the temple arm.

Side views of an embodiment of the integrative light monitor 10 (with and without the housing) are provided in FIGS. 5 and 6, where the printed circuit board 20, the microcontroller unit (MCU) 16, the power switch 18, the LEDs 12, the phototransistor 14, the battery 22, the battery holder 28, the battery access door 32, the capacitive touch plate 34, the ferromagnetic plates 36, the transparent front 26, the back 28 of the housing, and the bezel 30 are shown. The battery 22 can be advantageously mounted on an opposite side (e.g., a back side) of the printed circuit board from the other components or mounted in the clip or attachment mechanism 36, though the other components can be mounted essentially anywhere on the printed circuit board 20.

If the integrative light monitor 10 is to log light exposure over several days, then more than a single user input mechanism can be incorporated into the integrative light monitor 10 (e.g., more than a single capacitive touch plate 34) or the device 10 can be configured to recognize differentiating inputs (e.g., one tap versus two taps on the input mechanism for different inputs). The integrative light monitor 10 can include, e.g., multiple touch pads, push buttons 58 or an accelerometer 38 via which distinct motions can be differentiated), offering more than just the interrogate function, described above. Other commands that can be communicated via the user inputs include telling the integrative light monitor 10 to "start a session," "terminate a session," "re-initialize," (fresh start, clearing existing log) and optionally also "transmit" (e.g., if implemented in a scheme to transfer data to computer or cell phone).

The light detector can be in the form of a phototransistor 14, which is shown in FIGS. 4-7, or a series of phototransistors 14 that can respectively record radiation across different ranges of the electromagnetic spectrum. In one embodiment, the phototransistor 14 has dimensions of about 2 mm×1.25 mm measured parallel to the plane of the printed circuit board 20 and is surface mounted on the printed circuit board 20. The front 26 of the integrative light monitor's housing is transparent near its upper edge where the surface-mount phototransistor 14 is positioned so as to expose the surface-mount phototransistor 14 to incoming light. The transparent front 26 of the housing also makes the light emitting diodes (LEDs) 12, discussed below, visible through the housing 26 by the user. In additional embodiments, the detector 14 can be mounted to the printed circuit board 20 via extended leads. The leaded detector 14 can be mounted anywhere on the circuit board 20, and its long leads allow it to poke up through the front 26 of the housing. By poking through the housing 26, the leaded detector 14 is readily exposed to incoming light.

In other embodiments, a rechargeable cell battery can be used in place of the button-cell battery as the power supply 22. The rechargeable cell includes an electrical connector (e.g., a micro-USB port) for coupling the cell to a voltage source for recharging the battery 22. Use of a rechargeable battery 22 in the integrative light monitor design can ease design constraints aimed to limit demands on the battery 22. The rechargeable battery 22 can be recharged each night or during the day (or at least once a week) to keep the integrative light monitor 10 functioning. An advantage of using a rechargeable battery over a (non-rechargeable) conventional button-cell battery is that the integrative light monitor 10 would not need to be configured to be openable by a user to enable battery replacement.

Figure 14:
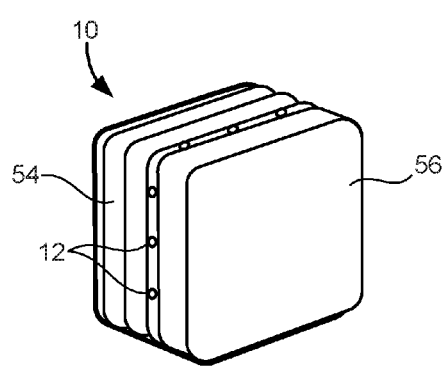
FIG. 14 is a perspective view of an integrative light monitor with a photovoltaic material acting as a light detector, or as a source of power, on its face.
Figure 15:
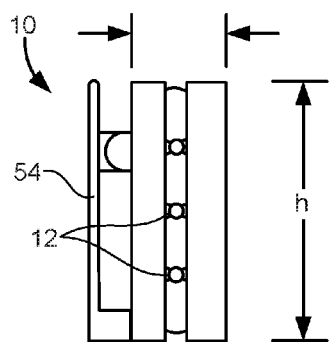
FIG. 15 is a side view of the integrative light monitor of FIG. 14.
Figure 16:
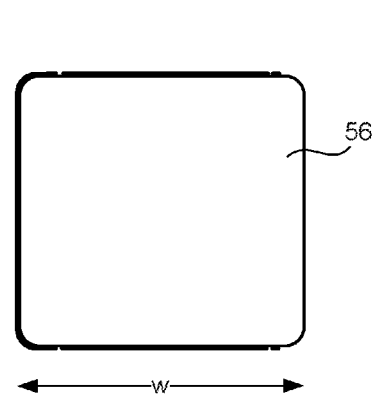
FIG. 16 is a front view of the integrative light monitor of FIG. 14.

In a particular embodiment, as shown in FIGS. 14-16, the light detector 14 comprises a photovoltaic material 56 (such as silicon) or an LED, or several photovoltaic materials connected in series; and the measured luminous flux is a function of the known area of the photovoltaic material 56 and either the current generated, voltage generated, some combination of current and voltage, or other property related to the absorption of photons by the photovoltaic material 56. In this embodiment, a portion of the electric current generated by the photovoltaic material 56 as a consequence of light exposure can be used as a supplemental power source or can be directed to the battery 22 to recharge the battery 22 for continued operation of the integrative light monitor 10. The photovoltaic material 56 in this embodiment has a square face with a width, w, and a height, h, of 20-30 mm, while the integrative light monitor 10 (excluding the clip 36) of 3-9 mm. As shown in FIGS. 14 and 15, the LEDs 12 can be positioned about the perimeter of the integrative light monitor 10, or they may be interspersed among individual photovoltaic materials on the face of the integrative light monitor 10.

Figure 17:
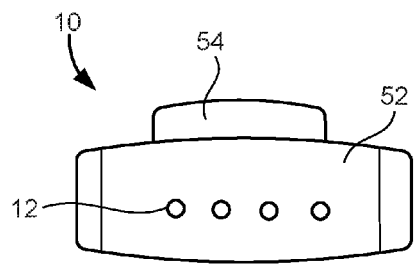
FIG. 17 is a top view of another embodiment of an integrative light monitor that includes a photovoltaic panel.
Figure 18:
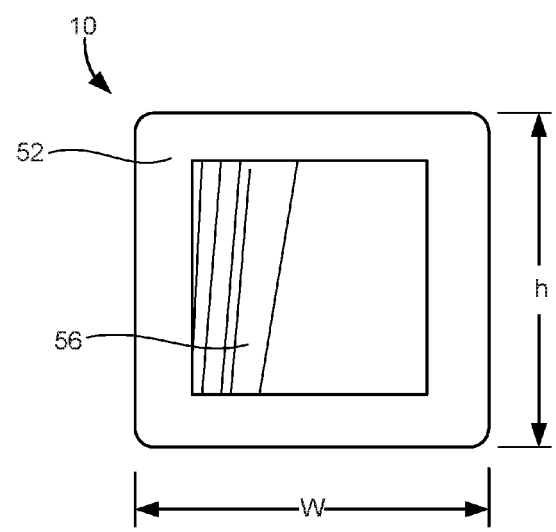
FIG. 18 is a front view of the integrative light monitor of FIG. 17.
Figure 19:
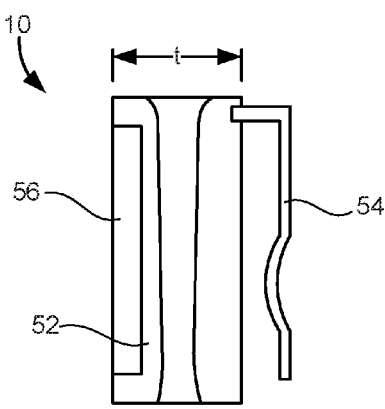
FIG. 19 is a side view of the integrative light monitor of FIG. 17.

In another embodiment, shown in FIGS. 17-19, a photovoltaic material 56, or several photovoltaic materials connected in series, acts as a detector 14 and, potentially, as a power source. In this embodiment, the photovoltaic material 56 is mounted in the casing 52 at the front face of the integrative light monitor 10; and the LEDs 12 can be mounted in the casing 52 about the perimeter of the integrative light monitor 10, or interspersed among individual photovoltaic materials 56 on the face of the integrative light monitor 10. The dimensions of the integrative light monitor 10 in this embodiment can be substantially the same as in the embodiment described in the previous paragraph.

Where the integrative light monitor 10 is provided with an on/off switch (e.g., in the form of a depressable or slideable power switch 18 on the edge of the integrative light monitor 10), the integrative light monitor 10 can also include a dim "On" LED indicator 12' among the LEDs 12 that illuminates to inform the wearer 42 that the battery 22 is being utilized and to help ensure that the wearer does not forget to turn it off after use (e.g., after bright light exposure is complete for the day or after the target exposure is reached). Use of the "On" LED indicator 12' is particularly advantageous when used in conjunction with the use of a rechargeable battery, since battery drainage may be less of a concern when the battery 22 can be easily recharged. Alternatively, the integrative light monitor 10 can be configured so that the LEDs 12 illuminate or blink in response to user input to indicate that the integrative light monitor 10 is on and responsive.

Moreover, whether using a rechargeable battery or an ordinary coin or button-cell battery 22, where the integrative light monitor 10 may be shut down during use, the integrative light monitor 10 can include nonvolatile memory; and the microcontroller unit 16 can be programmed to save the accumulated light-exposure value to the nonvolatile memory during power down (e.g., activated with the detection of a gradual decline in the supply voltage over, e.g., a period on the order of milliseconds). To facilitate this capacity for automatic saving of data, the integrative light monitor 10 can be designed so that power loss is drawn out over time during shutdown. In one embodiment, when the integrative light monitor 10 is restarted and power restored (e.g., by coupling with the reciprocal magnet or by activating the on/off switch 18), the microcontroller unit 16 can recall the accumulated light-exposure value and resume logging of light exposure (in its memory) toward the designated target exposure level. In this embodiment, where saving the light-exposure value is the default mode of operation, means for "resetting" the accumulated light exposure (e.g., at the start of a new day) can be provided, e.g., in the form of another button or via a coded activation of the button (e.g., depressing the button for multiple seconds, depressing the button multiple times or depressing multiple buttons simultaneously). If saving of the accumulated light exposure is not automated with powering down the integrative light monitor 10, a "save" button can be provided on the integrative light monitor 10 or a code for saving can be provided on one or more buttons shared with other functions. In these embodiments, the integrative light monitor 10 need not include a dedicated on/off switch 18 (or other mechanism), as the integrative light monitor 10 is powered and rendered operational by sun exposure on a photovoltaic material 56 or when power is available from an integrated battery.

The integrative light monitor 10 and associated electronics (e.g., a computer processor, memory and software non-transitorily stored on a computer-readable medium, as discussed below) measure both the instantaneous light-intensity and the integral of light-intensity over a period of time. Exemplary computer electronics and communication technologies that can be incorporated in or used with this integrative light monitor 10 are described in the sections entitled, "Computers, software, storage media and other components" and "Network connections and communications," below. The processor, which can be integrated into a microcontroller 16, can be coupled with the detector(s) 14. In particular embodiments, the processor can also be coupled with an accelerometer 38 and can record and integrate illuminance readings from the detector 14 to produce a cumulative luminous exposure value per instructions stored as software code on the computer-readable medium, which is also coupled with the processor (and which can also be incorporated into the microcontroller 16). Where an accelerometer 38 is used, its readings can be recorded and paired with the illuminance readings.

Pursuant to the software code processed by the processor, the processor compares the cumulative luminous exposure value with a chosen target value and communicates whether that target value has been reached or whether a particular increment toward that target value has been reached. That communication from the processor can be received, e.g., by a computer, cell-phone or custom display (e.g., LCD, E-Ink, etc.), by a bank of lights (e.g., LED's 12), an audio output (e.g., a speaker or bell), or a vibration mechanism (e.g., a piezoelectric plate) serving as a human interface to communicate the results to a wearer 42.

The integrative light monitor 10 can perform as a threshold device that will alert the wearer (e.g., through light activation, color change, or audible signal) when one of several states associated with medical/psychiatric benefits has been reached. The integrative light monitor 10 can register, for example, an exposure of 12-24 million lux-seconds. In particular embodiments, the target exposure is 18 million lux-seconds (e.g., exposure to 10,000 lux for 30 minutes or 2,500 lux for 120 minutes). Alternatively, or in addition, the integrative light monitor 10 can register, for example, an instantaneous exposure of 2,500 lux, to signify that the light intensity to which the user 42 is being exposed is sufficient to achieve medical/psychiatric benefits if maintained for sufficient duration. The integrative light monitor 10 can also generate a signal for UV exposure indicating, for example, (a) that the sun is sufficiently strong to produce vitamin D, (b) when the recommended vitamin D production has completed, or (c) when the user is likely to suffer a sunburn or other skin damage that may, for example, lead to melanoma or skin cancer.

These bright-light exposures can be used as therapy for various mood disorders, including major depressive disorder, which includes the presence of two or major depressive episodes (with an interval of at least two months between episodes). The major depressive episodes can be diagnosed, e.g., with a finding of the presence of five or more of the following symptoms during the same two-week period [representing a change from previous functioning and wherein at least one of the symptoms is either (a) depressed mood or (b) loss of interest or pleasure]:

1. depressed mood most of the day, nearly every day, as indicated by subjective report (e.g., feels sad or empty) or by observation made by others (e.g., appears tearful);
2. markedly diminished interest or pleasure in all, or almost all, activities most of the day, nearly every day (as indicated by subjective account or by observation by others);
3. significant weight loss when not dieting or weight gain (e.g., a change of more than 5% of body weight in a month), or decrease or increase in appetite nearly every day (or, in the case of children, a failure to make expected weight gains);
4. insomnia or hypersomnia nearly every day;
5. psychomotor agitation or retardation nearly every day (observable by others, not merely subjective feelings of restlessness or being slowed down);
6. fatigue or loss of energy nearly every day;
7. feelings of worthlessness or excessive or inappropriate guilt nearly every day, which is not merely self-reproach or guilt about being sick;
8. diminished ability to think or concentrate, or indecisiveness, nearly every day (either by subjective account or as observed by others); and
9. recurrent thoughts of death (not just fear of dying), recurrent suicidal ideation without a specific plan, or a suicide attempt or a specific plan for committing suicide.

Bright-light exposure can also be used to treat seasonal and non-seasonal depression. Bright-light exposure is also effective in the alleviation of subclinical seasonal mood changes ("winter blues") that are extremely common in populations that experience a significant decrease in sunlight during winter months. Additionally, exposure to bright light during the day [and prevention of bright-light exposure near (e.g., within an hour or several hours of) the time of sleep onset] can provide a beneficial effect in treating insomnia associated with circadian rhythm difficulties. Consequently, use of the integrative light monitor 10 in conjunction with light exposure by individuals with these conditions can also be advantageous. By signaling when a therapeutic "dose" is reached, the integrative light monitor 10 also allows the wearer 42 to limit excessive exposure to sunlight through the use of sun glasses and sunscreen at an appropriate time. In other embodiments, the integrative light monitor 10 can be used to treat, such as insomnia, attention-deficit hyperactivity disorder (ADHD), dementia in the elderly, bulimia nervosa, severe premenstrual syndrome, and bipolar disorder.

Figure 10:
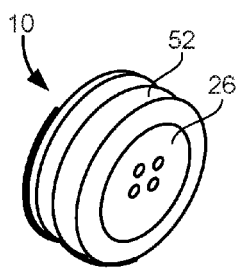
FIG. 10 is a perspective view of an integrative light monitor with four LED indicators.
Figure 11:
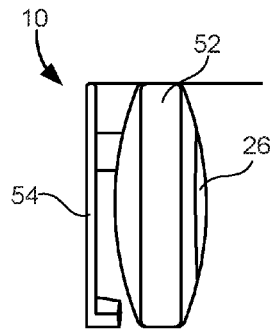
FIG. 11 is a side view of the integrative light monitor of FIG. 10.
Figure 12:
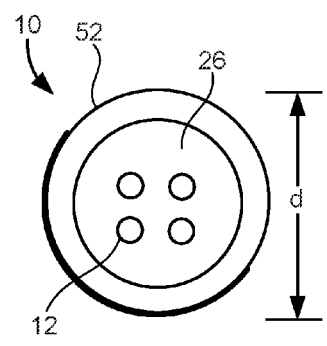
FIG. 12 is a front view of the integrative light monitor of FIG. 10.

In a particular embodiment, the integrative light monitor 10 can include a series of lights (e.g., four to six lights) in the form of miniature light-emitting diodes (LEDs) 12 arranged, e.g., in a half circle arch on a face of the integrative light monitor 10. Where four LEDs 12 are used, they can be arranged in a square pattern with one at each corner of the square like the configuration of holes found in a typical clothing button, as shown in FIGS. 10-12. In the integrative light monitor 10 of FIGS. 10-12, the LEDs 12 are covered by a transparent or frosted lens 26 mounted in a brushed aluminum casing 52 on the front face of the integrative light monitor 10. The integrative light monitor 10 also includes a clip 36 so that it can be clipped, e.g., to a user's clothing; and this embodiment of the integrative light monitor 10 can have a diameter, d, of 20-30 mm.

Where five lights 12 are provided for indicating cumulative exposure and where the target luminous exposure is 18 million lux-seconds, an additional LED 12 can light up with each incremental exposure of 3.6 million lux-seconds such that the full array of lights will be lit when the 18 million lux-second target is reached and the progress there toward can be incrementally monitored. The integrative light monitor 10 can also include a power on/off switch 18, which when activated (e.g., shifted or depressed), can initiate an electronic interrogation, wherein power from the battery 22 is confirmed (activating the power-indicating amber LED 12'), voltage from the battery 22 is measured for adequacy (triggering blinking of the LED's 12 if voltage is inadequate), and cumulative light exposure since startup is ascertained from the memory (turning on some or all of the LED's 12 to indicate the amount of light exposure). In an alternative embodiment, the switch 18 is a capacitive-touch switch built into the printed circuit board 20.

Figure 13:
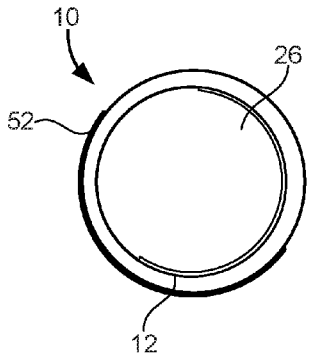
FIG. 13 is a front view an integrative light monitor with a radial LED ring that gradually illuminates around the perimeter of the window with increasing exposure to bright light.

In the embodiment of FIG. 13, the LED indicator 12 is in the form of a ring where sections of the ring sequentially illuminate with cumulative light exposure until the entire ring is illuminated, indicating that the target exposure is reached.

In one embodiment, the LED display 12 can be operated by depressing a push-button 58, which turns on an amber LED 12'; on the integrative light monitor, wherein the amber LED 12' remains lit to indicate that the integrative light monitor 10 is powered and operating properly. A plurality of green LEDs 12 on the integrative light monitor 10 sequentially turn on to indicate progress toward a light-exposure goal. In an embodiment with five progress LEDs 12, one lit progress LED 12 indicates ¼ completion; two lit progress LEDs 12 indicate ½ completion; . . . and five lit progress LED's 12 indicate that 125% of the exposure goal has been achieved. The fourth LED 12 (indicating 100% of the target dosage) can provide a distinctive light color (e.g., red) to provide a distinctive "completion" signal.

An additional indicator (e.g., LED) or a distinctive indication from the existing indicator(s) can be provided to indicate the intensity of the incident light (e.g., indicating whether it meets or exceeds 2,500 lux), as determined by the microcontroller 16, to thereby indicate whether, e.g., the intensity of the incident light is above a minimum threshold to produce a substantial benefit for the user; and the microcontroller 16 can be programmed to ignore incident light intensities below the minimum threshold and to only record intensities at or above the threshold.

The LED's 12 can be wired to remain activated to show progress for no more than several (e.g., three) seconds in response to the user activating the power switch/button 18 to preserve battery power. Alternatively, the LED's 12 can be configured to remain lit only if the power switch/button 18 is depressed. To warn a user of low-battery power, all LED's 12 can be programmed to blink or change color in response to the usual "display on" power switch/button activation.

In other embodiments, light exposure can be weighted as a function of time. Multiple studies have demonstrated that bright-light therapy for depression is most effective when administered in the morning and that early morning light is more effective than late morning light (bipolar disorder may be an exception, with perhaps a better response to mid-day light). Efficacy of the therapy is further increased if the timing of light therapy is adjusted based on an individual's circadian rhythm, either through measurements of melatonin peaks or through self-administered circadian-rhythm questionnaires. A log of the timing of light exposure allows the user, alone or in consultation with a clinician skilled in the use of light therapy, to maximize benefits of light exposure.

Figure 9:
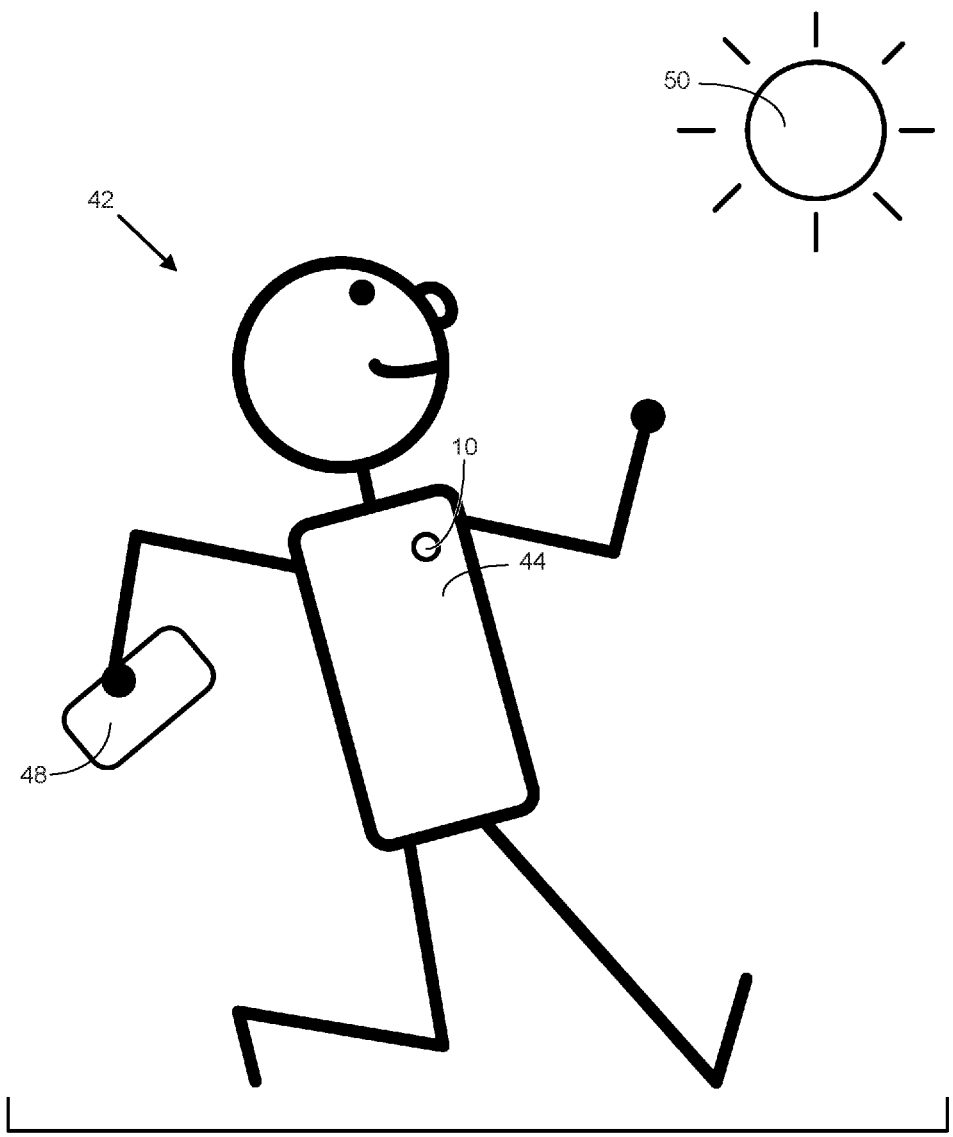
FIG. 9 is an illustration of a wearer of the integrative light monitor receiving light exposure from the sun, where the integrative light monitor is communicating with the wearer's smart phone.

Accordingly, in a method for monitoring light exposure through the eyes, the monitor records a time integral of exposure with accumulations time-stamped so as to make a record of the time-of-day when exposures occurred. These measurements may occur at regular intervals, e.g., every second, every minute, or timings in between, or at other irregular intervals that may be proportional to light exposure (i.e., more frequent readings taken in bright light or coinciding with other environmental factors). Accordingly, periodic readings of light exposure can be recorded in a database along with a current time stamp. This recorded data can be communicated to other electronic devices (e.g., to a smart phone 48; to "cloud storage" via the internet, via cellular data network, or via similar means and methods; or to a laptop, desktop or tablet computer) for remote display, processing and/or storage. An illustration of a user/wearer 42 of the integrative light monitor 10 10 (here, on his clothing 44) equipped with a smart phone 48 that is in (e.g., Bluetooth) communication with the integrative light monitor 10 as the wearer 42 is exposed to light from the sun 50 is provided in FIG. 9.

In additional embodiments for monitoring light exposure through a user's eyes, the integrative light monitor 10 or another electronic device 48 in communication with the integrative light monitor 10 receives input from the user 42 to indicate the timing and quantity of any supplemental treatments received by the user (e.g., supplemental products, such as melatonin, ingested by the user). In one embodiment, the user 42 inputs this information via a smart phone 48 using an "app" that includes instructions for requesting and receiving this information via an on-screen user interface. The smart phone 48 can be in wireless communication with the integrative light monitor 10, and the app or another software component, when executed by a processor, uses the input to better tailor the optimal light exposure for the individual user 42. If, for example, light therapy is working somewhat for a user 42, though not ideally, a mental healthcare provider can adjust the user's treatment program, e.g., by adding melatonin supplements or other supplements/drugs, such as anti-depressant drugs, to the treatment program. The user 42 can be instructed to ingest the melatonin supplements at a time that coincides optimally with the user's circadian rhythm. In other embodiments, the supplements can be taken to alter the user's circadian rhythm or to shift the optimal timing of exposure to bright light. In additional embodiments, use of the supplements can reduce the user's target bright-light exposure level.

In additional methods for monitoring light exposure through a user's eyes, physical activity is monitored concurrently using an accelerometer 38 or similar component(s) incorporated within the integrative light monitor 10, wherein the data from the accelerometer 38 or other component is fed to the computer processor. In this embodiment, the correlation between light exposure and physical activity can be used to better monitor and treat depression or other physical or mental illnesses. For example, detection of a high level of activity can be correlated with successful treatment, while detection of a low level of activity may trigger the medical provider to increase the targeted light exposure or to prescribe supplemental treatments in an effort to improve the user's condition. Moreover, in particular embodiments, the accelerometer 38 can also be used as an input device, as the user can flick or tap the device to indicate input.

In still more methods for monitoring light exposure through the user's eyes or on the user's skin, ultraviolet (UV) light is concurrently and separately measured by the integrative light monitor 10 (apart from concurrent measurements of total light exposure or of exposure to light in the, e.g., visible range) using a separate detector 40 (e.g., a UV photodiode) for the purpose of preventing harmful levels of UV exposure during light exposure that could lead to sunburn, skin cancer, etc. UV-light exposure approaching harmful levels can be communicated by making a mobile device beep; ring; vibrate; display a message; receive a text message, email, call, or other sort of notification; or via display in a mobile or computer application or on the device, itself.

Records of UV light exposure can also be used to determine and record what percentage of light exposure was obtained through natural sources, which may generate UV light, and artificial sources, which may not generate UV light. These correlations may, therefore, allow one to recognize that light exposure is from a natural source if UV light is concurrently detected or that light exposure is from an artificial source if no (or only smaller amounts of) UV light is detected when exposure to light at other wavelengths is detected. The user's program may be adjusted, for example, to target a higher ratio of natural light exposure, which may provide greater benefits than artificial light.

In one embodiment, a first detector 14 measures light exposure in the visible range (about 400 nm to about 700 nm) but not in the UV range (about 10 nm to about 400 nm), so it detects light from light boxes (which produce in the visible spectrum) as well as the visible-light portion of the radiation emitted from the sun 50, while the second detector 40 measures light in the UV spectrum but not in the visible spectrum. In this embodiment, the balance of light from artificial and natural sources is proportional to the cumulative exposures tallied from the first detector 14 and second detector 40, respectively.

In an alternative embodiment, either the first detector 14 or the second detector 40 detects light across both the visible and UV ranges, while the other detector detects light in only one of these ranges. Where, for example, the first detector 14 detects radiation across the visible and UV spectrums while the second detector 40 detects only radiation in the UV range, the cumulative exposure derived from readings from the second detector reflects cumulative exposure to sunlight. Meanwhile, cumulative exposure to light from artificial sources (e.g., light boxes) can be derived from the difference or ratio in cumulative exposure totals detected by the first and second detectors 14 and 40. In other embodiments, the detector 14 can have a design similar to the image detector of a VGA camera, where pixel resolution of red, green, and blue is possible with a single detector; or a series of filters that filter different wavelength ranges can be placed over parts or all of a detector.

Alternatively, or in addition, monitoring light exposure includes concurrent measurement of UV light by the second detector 40 to determine whether the UV light intensity is sufficient for vitamin D3 production. To determine whether the UV light intensity is sufficient, the integrative light monitor 10 can measure the UV index, for example, where a value above 3 is known to be sufficient. Appropriate light exposures may be, e.g., 10-15 minutes per day for three days a week, though the timings may be different depending on the user 42. Reaching the targeted UV exposure can be communicated by making a connected mobile device 48 (e.g., connected via Bluetooth or other form of wireless communication) beep; ring; vibrate; display a message; receive a text message, email, call, or other sort of notification; or by generating a display indication in a mobile or computer application (e.g., on a smart phone 48) or on the integrative light monitor 10, itself.

In particular embodiments, the integrative light monitor 10 and mobile phone combination ("device") can also be used to measure and track cumulative daily UV exposure for the purposes of estimating or calculating Vitamin D production and/or preventing sunburn. For Vitamin D production, the integrative light monitor 10 acquires knowledge of: (1) the user's skin type, (2) the percentage of the user's skin that is exposed, and (3) the cumulative UV exposure throughout the day. Sunburn prevention may only acquire (1) and (3).

The target UV exposure for Vitamin D production and/or sunburn depends significantly on skin type (e.g., melanin content, as most easily estimated by the darkness of the skin), so the user inputs skin color either by taking a photo of his/her skin using the integrative light monitor 10, or by selecting a particular color from a presented color gradient on the integrative light monitor 10. The input skin color is converted into one of the Fitzpatrick classifications, which range from I to VI. From this classification, the minimum erythemal dose (MED) would be obtained from published tables, such as those in Fitzpatrick's Dermatology in General Medicine (McGraw-Hill Professional; 5th edition). The MED is the point (in $mJ/cm^2$) at which one receives sunburn. MED varies significantly by skin type: a Fitzpatrick type II may have an MED of 38 $mJ/cm^2$, while a Fitzpatrick type IV may have an MED of 75 $mJ/cm^2$ (from Lo, et. al., Am J Clin Nutr, 1986). This MED sets the maximal daily exposure before sunburn.

For Vitamin D production, a dosage lower than the MED is desirable, as Vitamin D is produced before sunburn occurs when skin is subjected to UV light. Holick recommends ¼ MED on ¼ of skin per day (Holick, Am J Clin Nutr, 2004) for the medically accepted target of 1,000 International Units (IU). Users 42 can adjust the target in consultation with a medical specialist depending on the user's specific medical needs, or the user can use a different target, such as 400-800 IU, as recommended by the U.S. Food and Drug Administration. A different target would change the fraction of the MED or the fraction of skin exposed that functions as the daily target exposure for Vitamin D production.

To appropriately calculate Vitamin D production, the integrative light monitor 10 is also to be informed of the amount of skin that's exposed. Holick recommends ¼ MED on ¼ of total skin area. If less skin is exposed, the target fraction of MED may need to be increased, and vice versa. Percentage of skin exposed is calculated using the Lund-Browder chart, which assigns a percentage to each body part exposed. For example, one implementation of the Lund-Browder chart assigns the following values: face 3.5%, neck 2%, trunk 26%, hands 6%, arms 14%, legs 14%, and thighs 18%. These figures should be considered as being approximate. The percentage of skin exposed can be determined by any of the following: (a) direct percentage input by the user, (b) the user selecting from a series of cartoon images which depict people wearing various amounts of clothing that cover various amounts of skin, or (c) inferring the likely clothing worn by using GPS location in combination with the weather. For example, during July in Florida on a Saturday, a user 42 will likely be wearing shorts and a t-shirt exposing a significant amount of skin, perhaps in excess of 30%. However, during December in Boston, a user 42 will likely be wearing a heavy winter jacket and have very little skin exposed, perhaps as little as 3-4%.

The last component is to measure the accumulated UV radiation to which an individual is exposed on a daily basis. For example, a photodiode in the integrative light monitor 10 can be used to measure the UV radiation, and the intensity of that radiation can be logged as a function of time. Alternatively, radiation can be obtained by indirect measurement by, for example, utilizing measurements of the UV radiation from monitoring stations in the area (determined by GPS location of the integrative light monitor 10). Because UV radiation is highly directional, the indirect measuring method may be desirable. This indirect measurement can be achieved through something as simple as UV Index information obtained from a weather forecast provider (such as Weather Underground), measurements of UV radiation from other monitoring stations, or through a much more complex simulation of incident UV radiation, such as the FastRT program developed by Engelsen and Kylling. FastRT uses a number of variables including solar zenith angle, ozone column, aerosol loading, clouds, surface albedo, and surface altitude. These inputs can be determined by either a data source (monitoring station) located near the GPS location of the user 42 or by reasonable estimates given the time and season of the GPS location.

The effect of UV radiation is determined by applying an action spectrum, which assigns weightings to each wavelength of radiation within the UV spectrum. Two appropriate action spectra are the Commission Internationale de L'eclairage (CIE) action spectrum for the production of previtamin D3 in human skin (appropriate for Vitamin D calculations, CIE publication 174, 2006), or the CIE erythema action spectrum (appropriate for sunburn calculations). Other action spectra can also be applied, including ones that focus on the effect of UV-B radiation for Vitamin D production and on the combined effect of UV-A and UV-B for sunburn. Additional action spectra that rely on UV Index can also be used, for example, the one published by the World Health Organization (WHO).

For Vitamin D calculations, the selected action spectrum can then be applied to the measured, accumulated UV exposure; and the percentage of exposed skin can be used to calculate the total UV energy received. This value can be compared to the target exposure for Vitamin D production for a user's Fitzpatrick skin type.

For sunburn calculations, the selected action spectrum, which may be different from that used for Vitamin D, can be applied to the measured and accumulated UV exposure; and that value can be compared with the MED for a user's Fitzpatrick skin type.

The integrative light monitor 10 can also provide notifications and coaching. For Vitamin D production, the integrative light monitor 10 can inform of the following to the user 42: (a) when UV intensity is sufficient to produce Vitamin D, (b) how long the user will need to be in the UV light in order to reach the Vitamin D goal, (c) a percentage of progress toward the Vitamin D goal, and (d) a notification when the goal is reached, etc.

For sunburn prevention, the integrative light monitor 10 can inform the user 42 when accumulated UV intensity is sufficient to cause sunburn (a warning) and how much longer in UV light until the user will get sunburn, etc.

In other embodiments, the integrative light monitor 10 can include multiple light sensors, each equipped with a light filter to detect light in different wavelength bands (e.g., light of different colors). In this embodiment, a detector 14 configured to receive light from a filter that passes only blue light can, for example, be weighted higher (i.e., be multiplied by a greater weighting factor) than light detected by detectors 14 configured with respective light filters to receive light in other colors, as exposure to blue light may be more beneficial than exposure to light of other colors. Accordingly, the light exposure detected by each detector 14 can be multiplied by an appropriate weighting factor (determined by the efficacy of the respective wavelength band); and those multiples can be integrated until an overall daily target is reached.

Figure 22:
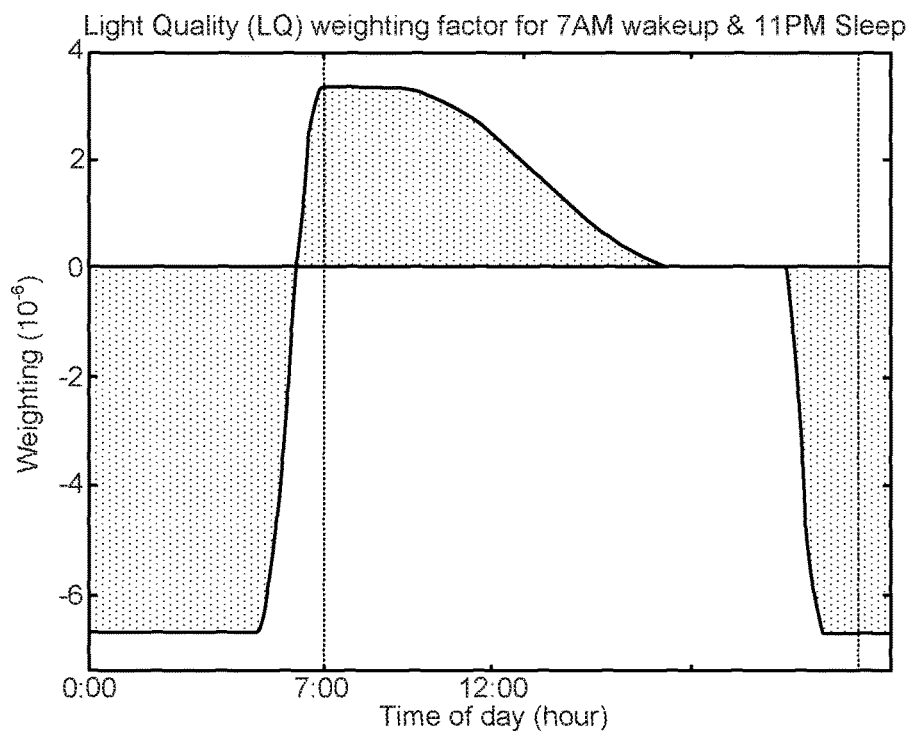
FIG. 22 is a plot of a light-quality weighting factor as a function of time of day.

In additional embodiments, data regarding daily integrated light exposure and data regarding the time of day of light exposure from the integrative light monitor 10 are used to calculate and display (e.g., on the display of another device 48, such as a computer, tablet or smart phone in communication therewith) a user's day-by-day rating of (1) actual light exposure as a percent/fraction of an optimal dose and (2) the closeness of fit between actual time of bright-light exposure and optimal timing of bright-light exposure. Standard optimal values for dosage (e.g., 10,000 lux for 30 minutes) or combinations of dosage and timing (e.g., 5,000 lux for 60 minutes within one hour of sleep offset) may be provided; or the values may be individualized based on treatment history and measures of circadian rhythm. An overall numerical score representing "light effectiveness" can be calculated, the components of which can include the percent/fraction of an optimal dose weighted by the time of day that the light was received and factored into measuring the user's progress toward an exposure target. For most people, light received within one hour before or after waking from sleep may be weighted with a factor of 1.0. Light received within another hour (an additional hour after sleep offset) may be weighted, e.g., at or close to 1.0, 0.9, 0.8, or 0.7. Light received during the day may be weighted with a factor of 0.0 if the incident intensity is less than a predefined brightness threshold (e.g., 2500 lux). Light further removed from sleep offset may be weighted less (e.g., at 0.5); and further out, such as in the evening, the light may be excluded by a weighting factor of 0.0. Light in the evening, e.g., within two hours of sleep and during sleep, may detract from the "light effectiveness" score (e.g., by having a weighting factor of −0.5, −1.0, −2.0, or even more negative). An exemplary unitless weighting function that assigns relative weight of measurements taken at different times of the day is described here and plotted graphically in FIG. 22.

1) If the time is more than two hours before wake time, the weighting is −2.0.

2) If the time, t, is within two hours before wake time, $t_{wake}$, the weighting, w, is given as:

$$w = \cos((t - t_{wake}) * \text{pi}/2) * \frac{3}{2} - \frac{1}{2}.$$

3) If the time is within two hours after wake time, the weighting is 1.0.

4) If the time, t, is more than two hours after wake time, $t_{wake}$, but more than 5 hours earlier than sleep time, $t_{sleep}$, the weighting, w, is:

$$w = \cos((t - t_{wake} - 2) * pi/(t_{sleep} - 5 - (t_{wake} + 2)))/2 + 0.5.$$

5) If the time is within 5 hours before sleep time but more than 2 hours before sleep time, the weighting is 0.

6) If the time, t, is 2 hours or less before sleep time, $t_{sleep}$, but more than 1 hour before $t_{sleep}$, the weighting, w, is:

$$w = -2 * \sin((t - (t_{sleep} - 2)) * pi/2).$$

7) If the time is not more than 1 hour before sleep time or is after sleep time, the weighting is −2.0.

8) The "light effectiveness" score is computed by multiplying each measurement of the incident intensity visible to the eye (in units of lux) by the value of the above unitless weighting function corresponding to the time at which the measurement was recorded and additionally dividing each measurement by a constant scaling factor having units of lux per measurement interval. An example of a constant scaling factor is 300,000 lux*min, which would result in a "light effectiveness" score of 10.0 if the user received 10,000 lux intensity light for 30 minutes within two hours after waking and received no light intensity at other times.

9) The unitless weighting function may be nonlinear as a function of incident light intensity for some or all of the measurement times. For example, a nonlinear version of #3 above may be rewritten as follows: if the time is within two hours after wake time and the light intensity is at or above 2,500 lux, then the weighting is 1.0; but if the light intensity is below 2,500 lux, then the weighting is 0. This change in weighting factor may increase or decrease linearly, quadratically, exponentially, logarithmically, or via some other relationship as a function of time-of-day. For some users, light exposure later in the day may be more beneficial than light earlier in the day. The relationship may be determined based upon dim-light melatonin onset (DLMO) of 10 pg/ml, 2 pg/ml, or other significant concentration, where the weighting factor can be 1.0 within an hour of DLMO, with decreasing effectiveness away from this time.

Another method of determining an optimal (or near-optimal) time of day for bright-light exposure is via user responses to circadian-rhythm questionnaires, such as the Morningness-Eveningness Questionnaire, which is a self-assessment described in Horne and Ostberg, "A self-assessment questionnaire to determine morningness-eveningness in human circadian rhythms," International Journal of Chronobiology, 4(2), 97-110 (1976). Again, the user 42 can be queried and can provide responses via a separate electronic device, such as a mobile phone or networked computer 48, in communication with the integrative light monitor 10. Examples of light-effectiveness or closeness-of-fit display methods include the following: (a) a graph with a bar indicating optimal timing of bright-light exposure and a bar indicating actual timing of bright-light exposure, (b) a digital or analogue display of the time interval between optimally timed completion of bright-light exposure and actual completion of bright-light exposure, (c) a calculation of percent overlap between optimal timing of bright-light exposure and actual timing of bright-light exposure, (d) a line graph of actual timing of bright-light exposure either superimposed or next to a line graph of optimal timing of bright-light exposure, or (e) other graphical representation of linear or non-linear mapping between optimal and actual timing of bright-light exposure.

In another embodiment, a wearable integrative light monitor 10 utilizes a temperature sensor to monitor the skin temperature of a peripheral appendage (e.g., the wrist skin temperature). An example of such a temperature sensor is the Thermochron iButton DS1921H (Maxim Integrated Products, Sunnyvale, Calif., USA). The temperature sensor may also be part of a circadian rhythm monitoring system [as described in Sarabia, J. A., Rol, M. A., Mendiola, P. & Madrid, J. A. Circadian rhythm of wrist temperature in normal-living subjects: A candidate of new index of the circadian system. *Physiol. Behav.* 95, 570-580 (2008)] that includes an apparatus with the following: a power source (e.g., a battery); a temperature sensor (e.g., a thermocouple); a computer processor coupled with the power source and in communication with the temperature sensor and configured to receive and record the temperature measured by the temperature sensor; an output device (e.g., a plurality of LED lights, a display screen, or a wired or wireless communication module for offloading data to a remote location) coupled with the computer processor; and a non-transitory computer-readable medium coupled with the computer processor and storing instruction code for analyzing the recorded temperature from the computer processor over time; and communicating a signal to the output device to generate and communicate a signal indicating that a particular point in the user's circadian rhythm (e.g., melatonin onset) has occurred or will occur in some specified time in the future (e.g., two hours in the future). The user 42 is thereby alerted of the optimal time to perform some action, such as increase or reduce the ambient lighting, obtain bright light, take a nap, prepare for sleep, wake up, or consume melatonin—containing dietary supplements.

The integrative light monitor 10 can also utilize the optimal circadian entrainment algorithm developed by Serkh and Forger [Kirill Serkh, et al., "Optimal Schedules of Light Exposure for Rapidly Correcting Circadian Misalignment," PLOS Computational Biology, Vol. 10(4): e1003523 (2014)] to minimize the disorienting effects of jetlag and night-time shift work. When a user travels across several time zones, jetlag is common as the user's circadian rhythm is out-of-sync with the new time zone. Similar disorienting effects can occur as a result of night-time shift work. Serkh and Forger's algorithm is based on the Switch Time Optimization (STO) method and calculates the optimal timing and duration of light exposure to effectively entrain the user's circadian rhythm to the desired cycle time in the quickest possible manner, thereby effectively mitigating the effects of jetlag.

In order to accommodate jetlag, the integrative light monitor 10 can either prompt the user 42 for starting and ending time zones, or determine this via a change in GPS location. To accommodate shift work, the integrative light monitor 10 can prompt for the current wake time and the desired wake time. The integrative light monitor 10 then calculates the optimal path for circadian rhythm entrainment via Serkh and Forger's algorithm. The integrative light monitor 10 then presents instructions to the user 42 that describe when to get light exposure and how much light to get. The integrative light monitor 10 can either continually, or at discrete times, recalculate these instructions based on the intensity of light received (or available) and the duration of light obtained, as measured by the integrative light monitor 10. The integrative light monitor 10 can function as a coach, providing notifications or alert to the user via a mobile phone 48 and interfacing with the built-in alarm clock on the mobile phone to set wake times, etc.

The integrative light monitor 10 can also utilize wrist temperature as: (1) an additional parameter, which is strongly related to circadian rhythm as described previously, (2) an input to the optimal entrainment algorithm, or (3) an indication of progress as compared with wrist temperature (circadian rhythm) from previous days. The user 42 can use this visualization to further tailor the desired end circadian rhythm.

Another method of determining an optimal (or near-optimal) time-of-day for bright-light exposure is to utilize data recorded by the integrative light monitor 10 to tailor the optimal timing and dosage of light exposure incorporated into the program for the specific user 42, which may include any of the following: (a) mood polls in which the user 42 participates via an external device 48, such as a smart phone or computer, where the recorded mood is correlated with contemporaneous light exposure; (b) data upload from the device 10/48 to a medical provider or other caretaker for remote monitoring and investigation of bright-light exposure, which can be sent via an external device 48, such as a mobile phone, computer, or other means; (c) data summaries of bright-light exposure, where the data summaries are published or shared with others via social media or similar sites to encourage the user 42 through behavioral reinforcement (e.g., positive feedback) or contact with friends, family, or other important people; and/or (d) presentation of rewards to the user 42 or other reinforcement mechanisms to encourage the user 42 to obtain the optimally targeted light exposure.

In yet another method, data recorded by the integrative light monitor 10 is communicated and utilized such that the user's medical provider or other person administering or monitoring treatment can remotely monitor the user's compliance with the treatment, including monitoring the amount of light received per day, the time that the light was received, the user's physical activity level, the user's exposure to particular types of light (e.g., ultraviolet), and/or the user's mood, feelings, or other physical or mental characteristics. Where exposure to ultraviolet light is detected, that exposure can be correlated with exposure to natural (sun) light, as artificial light from light boxes typically is entirely or nearly entirely within the visible light range. In additional embodiments, this data is shared with friends (e.g., via social media) or otherwise updated to a website or other online platform viewable by others to generate additional motivation for the user 42.

Moreover, the data stored in memory on the integrative light monitor 10 can be communicated and utilized such that the medical provider or other person administering or monitoring treatment (e.g., via a smart phone 48) can remotely alter the user's treatment plan, communicate with the user 42, or provide other forms of information based on the data collected by the integrative light monitor 10 to (1) increase the user's target light dosage, if found to be insufficient; (2) decrease the user's target light dosage, if found to be excessive; (3) alter the user's targeted optimal time of day to receive light, which can be moved earlier or later, depending on the user's response; (4) coordinate or suggest other forms of medication or supplements for the user 42, such as anti-depressant medication, melatonin supplements, or others; (5) schedule or monitor the user's activity, which can include general daily activity or exercise; (6) schedule or suggest a follow-up exam, phone conversation, chat, email, or other mode of conversation between the user 42 and provider.

In other embodiments, an electronic display (e.g., such as those manufactured by E Ink of Cambridge, Mass.) can be used to display light exposure measurements and other indicators in place of the LED's, described above. Using an E Ink display, where colors or darkness levels in pixelated regions in a display area can be established by attracting pigment that is dark or light (or of a particular color) within microcapsules via application of an electric field, which enables very low-energy operation. While other embodiments may only activate the indicators/display when "interrogated" via an activation from the user 42 (to save power), a zero-power display, such as those manufactured by E Ink, allow for continuous display.

The integrative light monitor 10 can have a simple construction and can be relatively inexpensively produced; and eliminating the uncertainty of dosing allows sunlight exposure to safely, easily, and enjoyably replace the tedium of sitting at a desk or table tethered closely to a light box. The integrative light monitor 10 can, however, also respond to artificial light of sufficient intensity, allowing the wearer to move freely between artificial and natural light while continuing to monitor adequate light exposure. If, for example, a wearer 42 sits in front of a light box at 10,000 lux for 15 minutes and also is subject to an additional 9 million lux-seconds of light exposure while, e.g., walking to work on a sunny day, the integrative light monitor 10 can sum those exposures and accurately determine that the cumulative exposure satisfies a 18 million lux-seconds target. The integrative light monitor 10 can be packaged with an instruction sheet that explains proper timing of light exposure for optimal benefits and the potential side effects of excessive light exposure. Alternatively, instructions can be conveyed via the software/app that is operated in communication with the integrative light monitor 10 and that is viewed by the user 42.

In various embodiments, the integrative light monitor 10 can communicate the light-exposure data to other external electronic components (e.g., to a smart phone 48, to "cloud storage" via the internet, or to a laptop, desktop or tablet computer) for remote display, processing and/or storage. The data can be communicated via an integrated communication device (e.g., a wireless transmitter, which can include and utilize near-field technology or low-energy Bluetooth technology, or a USB port) in the integrative light monitor 10.

In particular embodiments, the integrative light monitor 10 can connect, not only to a computing/communication device 48, such as a mobile phone or computer, but also to either a light box or other source of bright light within the home or elsewhere using Bluetooth transmitters/receivers, another wireless technology, or some proprietary protocol, wherein the light box or other light fixture responds to the integrative light monitor 10 with specificity as to the person using the identified integrative light monitor 10. For example, the light box can be programmed automatically to turn on if the integrative light monitor 10 indicates that a user 42 (associated with the integrative light monitor 10) has obtained insufficient light exposure (i.e., has not yet reached a targeted threshold for bright-light exposure); similarly, the light box can be programmed to beep or blink to remind the user 42 to use light therapy. These methods can work the same way for a light fixture within a home; for example, a ceiling light in the kitchen or bathroom could switch to "bright mode" if it detects a integrative light monitor 10 associated with a user 42 in the area with insufficient light exposure. Such integrated fixtures can eliminate the separate need for a light box.

In additional embodiments, a wearable light monitor for visible light of therapeutic intensity (e.g., visible light of 2,500 lux or greater) is configured to be powered by the light that it senses. This light monitor can additionally sense the amount of UV radiation, while being powered by the light that it senses. Consequently, the light monitor can be operated for days, weeks, years, etc., without ever (or only rarely) needing to be connected with an external voltage source for recharging. The light monitor can use a single electronic element to both harvest energy from the incident light and to sense the intensity of the incident light; or it may use two separate elements for these functions. For example, the energy collecting unit may be a solar module made of single crystal silicon and the light sensing unit may be a conventional silicon photodiode.

In embodiments where two or more photo-responsive elements having different optical responsivities are included in the monitor and used to sense incident light intensity, the measured intensities as sensed by these elements can be combined to determine the nature of the light source. For example, one photo-responsive element may be sensitive only to visible light (e.g., a conventional silicon photodiode with a filter designed to mimic the responsivity of the human eye) and an additional element may be sensitive to both visible and near-infrared light (e.g., a solar module made of single crystal silicon). If the intensity as measured by both elements is equal or nearly equal, then a determination can be made that the light was not produced by a standard tungsten-filament light bulb, which generates a significant amount of near-infrared light. For example, the respective intensities from the photo-responsive elements may be used to determine if the incident light was sunlight or if it originated from a fluorescent lamp.

The wearable light monitor can transmit the light intensity data to a smart phone 48 (including a processor and memory and running an operating system, loaded with apps, and in communication with the internet) or other computing device using a low-power wireless protocol, such as Bluetooth Smart, such that the total power expended in sensing light intensity and transmitting the light intensity data to the computing device is less than the power harvested from the light that is sensed.

The sampling frequency e.g., how often the light intensity is measured) can be adjusted to govern the amount of energy consumed by the integrative light monitor 10. For example, the sampling frequency can be reduced if/when battery power is running low. Additionally, the rate at which communications (e.g., Bluetooth Smart communications) from the light monitor are advertised (e.g., broadcasting or connecting with a smart phone 48). For example, if the integrative light monitor 10 is not in bright light, it only advertises when the user presses the button 58. When the light monitor is in light with an intensity greater than, e.g., 2,500 lux, the integrative light monitor 10 can advertise once per minute. Consequently, relevant data (when the incident light is sufficiently bright) can be transferred in near real time.

Figure 20:
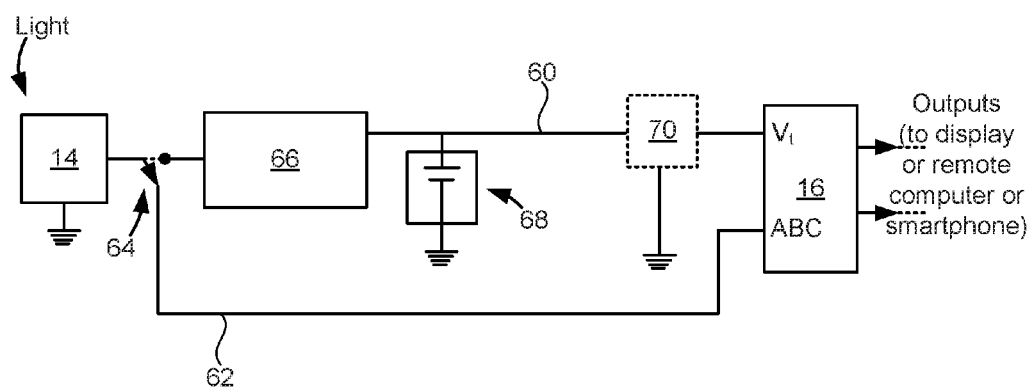
FIG. 20 is a schematic illustration of a circuit for a dual-purpose light recording and harvesting apparatus in the integrative light monitor, where incident light is converted to electricity that is recorded to track incident light and also utilized to power the device.

The wearable light monitor, as shown in FIG. 20, can include the following:

1) a light sensor 14 (e.g., a photovoltaic cell—i.e., a device that generates electric current when illuminated with light); the light sensor 14 can be fabricated to have a sensitivity matching that of the human eye;
2) microcontroller 16;
3) a first conductive pathway 60 electrically connecting the light sensor 14 with the microcontroller 16 to power the microcontroller;
4) a second electrically conductive pathway 62 connecting the light sensor 14 with the microcontroller 16 to provide a current flow from the light sensor 14 to enable the microcontroller 16 to measure the current flow, from which the intensity of incident light on the light sensor 14 can be extrapolated;
5) a load switch 64 configured to control the flow of electric current produced by the light sensor 14 to the first conductive pathway 60 and to the second conductive pathway 62 and to switch from one to the other;
6) an energy harvester 66 in the first conductive pathway 60, wherein the energy harvester 66 is configured to step up the voltage of the electric current from the light sensor 14;
7) an energy-storage device 68 (e.g., a battery or supercapacitor) for storing energy when fed with the electric current from the energy harvester 66 in the first conductive pathway 60;
8) a regulator 70 in the first conductive pathway 60, configured to regulate the flow of electric current (or voltage, as these terms may be used interchangeably here) from the energy-storage device 68, wherein the microcontroller 16 is in electrical communication with the regulator 70 and receives electrical current from the regulator 70 to power the microcontroller 16;
9) a wireless transmitter that transmits light-exposure data from the microcontroller 16 to a phone or computer 48 for analysis and storage of the data; the protocol (e.g., Bluetooth Smart) used by this component is low power and consumes less power than is harvested and stored in the energy storage device 68; the wireless transmitter is electrically coupled with the regulator 70, as well; and
10) optionally, additional electrical components e.g., an output device 12, such as LEDs) can also be in electrical communication with the regulator 70, wherein the regulator 70 controls the distribution of power to each of the components, as needed.

The energy harvester 66 is a switching voltage regulator that uses an inductor to boost a low input voltage up to a voltage sufficient to power the electronics of the integrative light monitor 10, most of which may be in the microcontroller 16. In a particular embodiment, the output of two photovoltaic cells 14 in series and in the 1-volt range are stepped up to about 3.7 V, the nominal voltage of a rechargeable lithium polymer battery used as the energy-storage device 68. The energy harvester 66 can be designed to adjust its loading to keep the input close to a maximum power, where voltage and current from the photovoltaic cells 14, $V_{pv}$ and $I_{pv}$, form a maximal product, while also preventing over-charging of the energy storage device 68.

Figure 21:
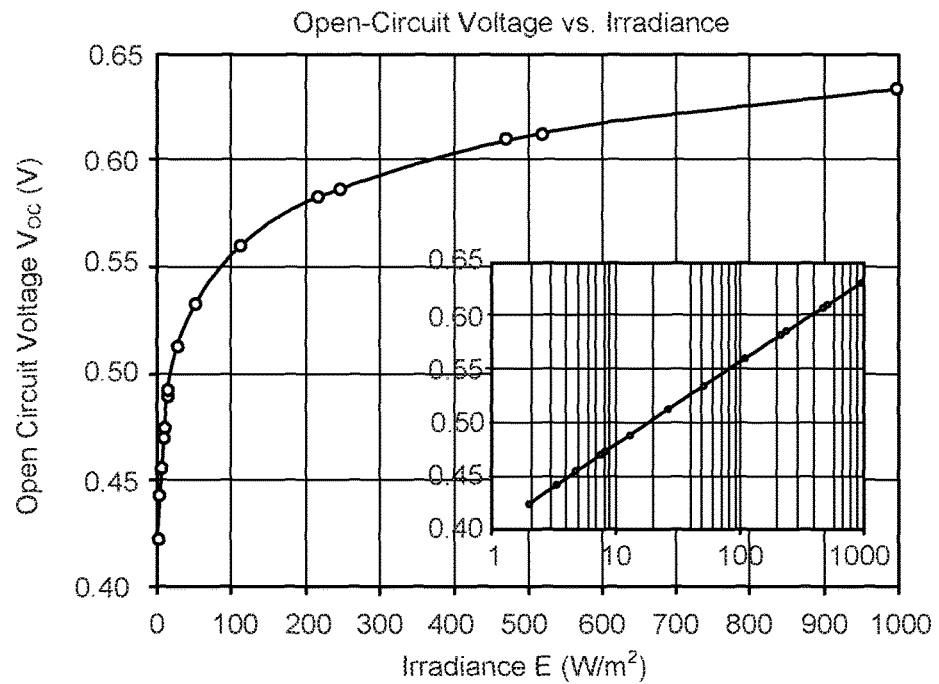
FIG. 21 is a plot of open-circuit voltage versus irradiance captured by the integrative light monitor.

The relation between the intensity of incident light on the light sensor 14 and the open circuit voltage is plotted in FIG. 21. Based on the function revealed by this plot, the microcontroller 16 can linearize and calibrate the electric current measurements to determine the intensity of the incident light on the light sensor 14. In particular embodiments, the electric current/light intensity measurements are made while the first conductive pathway 60 is disconnected via the load switch 64 (which can be a MOSFET or analog switch toggled by the microcontroller) from the photovoltaic cell so as to prevent loading from distorting the measurement.

A plurality of the light monitors 10 used by different people in different locations enables the creation of a distributed sensor network that collects solar information (e.g., solar intensity data), bright light usage, ambient lighting levels, and/or other light-related health information over local or global ranges.

In one embodiment, the mechanism by which this sensor network operates is that the distributed sensors communicate information to a local base station, which can be a mobile phone or other mobile device 48, or a computer located nearby; or the sensor can send information wirelessly to a remote computer or mobile device. The method of information transfer can include Bluetooth, Bluetooth Smart (Bluetooth 4.0), wi-fi, or a cellular network. The transmission protocol and frequency is designed to be low-power, as described previously.

Once the data arrives at the local or remote base station, the data is then uploaded to a database, cloud server, or something similar. Thus, the collected data can now be analyzed and/or shared by the base station. Analyzed data can be used, in conjunction with geo-location data (provided by the local computing device 48), to identify trends that are specific to different regions of the world, which can include daily light exposure, daily solar intensity, and indoor light conditions. From this data, public health officials can therefore make determinations as to areas at risk for light-related conditions, such as Vitamin D deficiency or Seasonal Affective Disorder. On a more individual level, a single user's data can be compared with his/her peers' data to determine if the light exposure received by a specific individual is significantly above or below the average light exposure for the particular region. This determination can provide targeted feedback and/or warnings to specific users that they might be at risk for light-related health conditions, such as Vitamin D deficiency or Seasonal Affective Disorder, and can provide a basis for remote medical intervention. Such a sensor network can also be used to treat and monitor people with an existing light-related medical condition and to determine the effectiveness of lifestyle changes in comparison with others nearby.

This distributed sensor network can also provide predictive analytics to those who are interested in light exposure, regardless of whether or not they are using a light monitor 10. For example, if there are five active monitors 19 in Neighborhood A, each registering 10,000 lux, another person in Neighborhood A can check the app or website that interfaces (directly or indirectly) with the light monitor 10 to instantaneously know the brightness level outside, along with a prediction as to how long the person would need to be outside in order to achieve his/her daily light dosage. On the other hand, excessive UV intensity can also be monitored, and warnings can be issued to individuals based on the estimated time to sunburn or skin damage. The system can function similarly to how GPS-enabled smartphones provide traffic data, which improves the predictions of mapping services in estimating time-of-arrival based on real-time traffic information.

In additional embodiments, a user can upload his or her light exposure/intensity data to a peer or social network (e.g., Facebook, Google Plus, LinkedIn, Twitter, etc., or a peer network established expressly for this purpose), where that data can be shared and exchanged with other users. Accordingly, one user can compare his/her light exposure data with that of a friend in a competitive and collaborative fashion (e.g., where the users compete against one another in terms of meeting exposure targets or where they compete collaboratively as teams to meet those goals). Likewise, one user's data can be monitored by another to provide feedback or support.

In yet another embodiment, light intensity data that is uploaded with location-specific coordinates (e.g., solar panel arrays that load their production data, e.g., in kilowatts or kilowatt-hours, which can be converted into light exposure readings using the known parameters of the solar array) can be used in combination with or as alternative to the location-based light exposure data received from multiple light monitors 10 to establish a light-intensity map that can be communicated to users 42. Light-intensity data from other sources, such as weather stations, can likewise be integrated into the system to produce the light-intensity map.

Computers, Software, Storage Media, and Other Components

The systems and methods of this disclosure can be implemented in a computing system environment. Examples of well known computing system environments and components thereof that may be suitable for use with the systems and methods include, but are not limited to microcontrollers 16, personal computers, server computers, hand-held or laptop devices, tablet devices, multiprocessor systems, microprocessor-based systems, set top boxes, programmable consumer electronics, network PCs, minicomputers, mainframe computers, distributed computing environments that include any of the above systems or devices, and the like. Typical computing system environments and their operations and components are described in many existing patents (e.g., U.S. Pat. No. 7,191,467, owned by Microsoft Corp.).

The methods may be carried out via non-transitory computer-executable instructions, such as program modules. Generally, program modules include routines, programs, objects, components, data structures, and so forth, that perform particular tasks or implement particular types of data. The methods may also be practiced in distributed computing environments where tasks are performed by remote processing devices that are linked through a communications network. In a distributed computing environment, program modules may be located in both local and remote computer storage media including memory storage devices.

The systems (e.g., of the "client" and "server") and methods of this disclosure may utilize a computer (e.g., in the form of a microcontroller 16) to carry out the processes described herein. Components of the computer may include, but are not limited to, a computer processor, a computer storage medium serving as memory, and coupling of components including the memory to the computer processor. A microcontroller 16 is a small computer including a single integrated circuit containing a processor core, non-transitory computer storage media (memory), and programmable input/output peripherals and can be used as an embedded system. The microcontroller 16 memory can include both permanent (nonvolatile) read-only memory (ROM) storing pre-programmed software in the form of a compact machine code as well as volatile read-write memory for temporary data storage. The microcontroller 16 can also include an analog-to-digital converter if the light detector 14 to which it is electronically coupled transmits its illumination data in analog format as well as a programmable interval timer to control, e.g., the duration of activation of the indicator LEDs 12.

The various processes described in the descriptions of this disclosure can be encoded as software instructions in memory and executed by a processor to carry out the processes.

Network Connections and Communications

The computing device 48 (e.g., computer or smart phone) can operate in a networked environment using logical connections from a server to one or more remote client computers (e.g., microcontrollers 16 embedded in discrete integrative light monitors 10). The remote computer can be a personal computer, a server, a router, a network PC, a peer device or other common network node, and typically includes many or all of the elements described relative to the above-described computer. The networked environment can include a local area network (LAN), a wide area network (WAN), and/or other networks. Such networking environments are commonplace in offices, enterprise-wide computer networks, intranets and the internet.

When used in a LAN networking environment, the computer can be connected to the LAN through a network interface or adapter. When used in a WAN networking environment, the computer can include a modem or other communication interface for establishing communications over the WAN (e.g., over the internet). The communication interface, which can be internal or external to the computer housing, can be connected to the system bus via the user-input interface or other appropriate mechanism.

In an embodiment of a WAN environment, light-exposure data from the integrative light monitor 10 can be uploaded via a transmitter and the internet to a computer server; and a user 42 (via a client computing device 48 connected with and in communication with the internet) accesses that data using, e.g., an internet browser (such as Internet Explorer from Microsoft, Firefox from Mozilla, or Chrome from Google) via hypertext transfer protocol (HTTP) communications or via communications generated and/or received by a software program, such as an email application (e.g., Microsoft Outlook) that can be stored in the computer's memory. The computer server can be a computer including memory storing a web server application, such as the Apache HTTP Server. The client computer can send an HTTP GET request to the server via the communication media that form the internet, and the participating server can respond to the client computer via the internet with an appropriate HTTP response.

HTTP is a request-response protocol standard for client-server computing. In HTTP, a personal computer running a web browser, for example, acts as a client, while a computer hosting a web site acts as a server. The client submits HTTP requests to the responding server by sending messages to it. The server, which stores content (or resources) such as HTML files and images, or generates such content on the fly, sends messages back to the client in response. These returned messages may contain the content requested by the client or may contain other kinds of response indications. Between the client and server, there may be several intermediaries, such as proxies, web caches or gateways. In such a case, the client communicates with the server indirectly and only converses directly with the first intermediary in the chain.

An HTTP request message from the client can include the following: (a) a Request line that requests a resource (such as an image); (b) Headers; (c) an empty line; and, optionally, (d) a message body. The HTTP Headers form the core of the HTTP request, as they define various characteristics of the data that is requested or the data that has been provided. The HTTP Headers can include a referrer that identifies, from the point of view of an internet webpage or resource, the address of the webpage (e.g., the URL) of the resource that links to it. By checking the referrer, the new page can determine the source of the request message. A variety of different request protocols exists; for example, a "GET request" requests a representation of the specified resource from the host.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/1000^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A method for monitoring light exposure, comprising:
   receiving light exposure from at least one light source with a light detector of a light monitor, wherein the light monitor further includes at least one of (a) an output device and (b) a communication device transported by a user;
   using the light detector to convert the light exposure into an electrical signal;
   recording current time of day as the light exposure is received;
   generating an instantaneous light exposure value from the electrical signal;
   applying a weighting function to the instantaneous light exposure value as a function of the recorded time of day associated with the light exposure to produce a weighted instantaneous light exposure value;
   integrating the weighted instantaneous light exposure value to produce a weighted cumulative luminous exposure value;
   comparing the weighted cumulative luminous exposure value with an established luminous-exposure target; and
   providing an indication of the weighted cumulative luminous exposure value in comparison with the established luminous-exposure target.

2. The method of claim 1, wherein the luminous-exposure target is in the range of 12-24 million lux-seconds.

3. The method of claim 1, further comprising applying a minimum light-intensity threshold to the light exposure to exclude illuminance below the minimum light-intensity threshold.

4. The method of claim 1, further comprising:
   receiving input regarding at least one supplemental factor selected from (a) supplemental treatment received by the user and (b) user physical activity; and
   determining and communicating luminous exposure targets to the user based, in part, on the supplemental factor.

5. The method of claim 1, further comprising separately measuring and recording exposure to radiation in different wavelength ranges.

6. The method of claim 5, further comprising separately measuring and recording exposure to blue light.

7. The method of claim 5, wherein separate detectors respectively measure exposure to light in the visible wavelength range and in the ultraviolet wavelength range.

8. The method of claim 7, further comprising identifying recorded light exposure that is received when ultraviolet radiation exposure is also received as being sourced from natural sunlight.

9. The method of claim 7, further comprising evaluating the measured ultraviolet radiation exposure to estimate production of vitamin D3 by the user due to the user's light exposure.

10. The method of claim 9, further comprising evaluating the measured ultraviolet radiation exposure to estimate risk of the user suffering sunburn due to the user's light exposure.

11. The method of claim 7, further comprising factoring at least one of (a) the user's skin type or (b) the amount of the user's skin that is exposed in calculating effects of the user's light exposure.

12. The method of claim 1, wherein the modification is provided by applying a light-quality weighting factor to the recorded light exposure.

13. The method of claim 12, wherein the light-quality weighting factor is correlated with the user's circadian rhythm.

14. The method of claim 1, further comprising providing an indication of the instantaneous light exposure value in comparison with the established instantaneous light exposure target.

15. The method of claim 14, wherein the established instantaneous light exposure target is in a range from 2,500 to 10,000 lux.

16. The method of claim 1, wherein the light detector includes a photovoltaic cell that converts the light exposure into electric current, the method further comprising:
- directing at least some of the electric current from the photovoltaic cell through a first conductive pathway to an energy harvester that increases the voltage of the electric current to produce a stepped-up current;
- directing the stepped-up current into an energy-storage device;
- extracting electric current from the energy-storage device; and
- delivering the extracted electric current to electrical components in the light monitor to power the electrical components.

17. The method of claim 16, wherein the electrical components powered by the extracted electric current include at least one component selected from the following: a microcontroller; a wireless transmitter; a wireless receiver; and an output device that provides the indication of the cumulative luminous exposure value.

18. The method of claim 1, further comprising transmitting at least one of cumulative and instantaneous light exposure data from the light monitor to a computing device that collects uploaded data from multiple integrative light monitors in different locations.

19. The method of claim 18, further comprising wirelessly receiving information from the computing device about the data from integrative light monitors.

20. The method of claim 1, wherein the indication of the weighted cumulative luminous exposure value is provided actively and directly to the user from at least one of:
(a) the output device; and
(b) a mobile device transported by the user and in communication with the communication device.

21. The method of claim 20, wherein the output device comprises at least one of a display screen and a light indicator, and wherein the indication of the cumulative luminous exposure value is provided to the user by the display screen or light indicator of the output device.

22. The method of claim 20, wherein the indication of the cumulative luminous exposure value provided to the user by the mobile device, wherein the mobile device is a smart phone.

23. The method of claim 1, wherein the light exposure received by the light monitor and converted to the electrical signal comprises visible light.

24. A light-monitoring system including an apparatus comprising:
- a power source;
- a light detector that generates an electrical signal when illuminated by light;
- a computer processor coupled with the power source and in communication with the light detector and configured to receive and record an indication of exposure to light from the generated electrical signal;
- an output device coupled with the computer processor and configured to communicate directly with a user of the light monitoring system; and
- a non-transitory computer-readable medium coupled with the computer processor and storing instruction code for summing the recorded indication of exposure to light from the computer processor over time and communicating a signal to the output device to generate and communicate a signal to the user of the light-monitoring system indicating that a cumulative threshold light exposure for the user to achieve a psychological benefit or a benefit in treating insomnia or a circadian rhythm disorder has been reached.

25. The light-monitoring system of claim 24, further comprising an output device coupled with the computer processor, wherein the output device provides an indication of at least one of cumulative and instantaneous light exposure.

26. The light-monitoring system of claim 24, wherein the light detector has multiple different spectral responsivities to allow determination of the source of the incident light.

* * * * *